(12) United States Patent
Bloom et al.

(10) Patent No.: US 7,815,673 B2
(45) Date of Patent: Oct. 19, 2010

(54) DOUBLE-WALLED STENT SYSTEM

(75) Inventors: Eliot Bloom, Hopkinton, NH (US); Gian Pellegrini, Santa Rosa, CA (US); Juan-Pablo Mas, Cambridge, MA (US); Nasser Rafiee, Andover, MA (US); Morgan House, Newfields, NH (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 119 days.

(21) Appl. No.: 12/060,332

(22) Filed: Apr. 1, 2008

(65) Prior Publication Data

US 2009/0248132 A1    Oct. 1, 2009

(51) Int. Cl.
*A61F 2/06* (2006.01)

(52) U.S. Cl. .................. 623/1.15; 623/1.16; 623/1.24

(58) Field of Classification Search ............ 623/1.12, 623/1, 15, 1.16, 1.17, 2.11, 1.24, 1.15
See application file for complete search history.

(56) References Cited

U.S. PATENT DOCUMENTS

| | | | |
|---|---|---|---|
| 5,064,435 A | | 11/1991 | Porter |
| 5,591,197 A | * | 1/1997 | Orth et al. ............ 623/1.16 |
| 5,843,167 A | * | 12/1998 | Dwyer et al. ............ 623/1.14 |
| 5,957,949 A | | 9/1999 | Leonhardt et al. |
| 6,425,916 B1 | * | 7/2002 | Garrison et al. ............ 623/2.11 |
| 2003/0204245 A1 | | 10/2003 | Brightbill |
| 2005/0192662 A1 | | 9/2005 | Ward |
| 2006/0287706 A1 | | 12/2006 | Olsen et al. |
| 2007/0073373 A1 | | 3/2007 | Bonsignore |
| 2008/0262593 A1 | * | 10/2008 | Ryan et al. ............ 623/1.12 |
| 2008/0262598 A1 | | 10/2008 | Elmaleh |

FOREIGN PATENT DOCUMENTS

| | | |
|---|---|---|
| WO | WO96/33672 | 10/1996 |
| WO | WO01/34064 | 5/2001 |
| WO | WO2004/021929 | 3/2004 |
| WO | WO2007/149933 | 12/2007 |

* cited by examiner

*Primary Examiner*—Corrine M McDermott
*Assistant Examiner*—Matthew Schall

(57) ABSTRACT

A double walled stent system particularly suited for treating abnormalities of the right ventricular outflow tract is disclosed having an exterior stent component and an interior stent component. The exterior stent component includes a plurality of longitudinally-extending connectors such as straight or sinusoidal bands. The interior stent component has a generally tubular cylindrical body and is centered within the exterior stent component. The stent system has a contracted delivery configuration and a radially expanded configuration for contacting the vessel wall. When deployed, the longitudinally-extending connectors of the exterior stent component come in contact with the vessel wall and fix the stent system to the treatment site. The interior stent component also radially expands but remains centered inside the exterior component and makes little to no contact with the vessel wall.

19 Claims, 30 Drawing Sheets

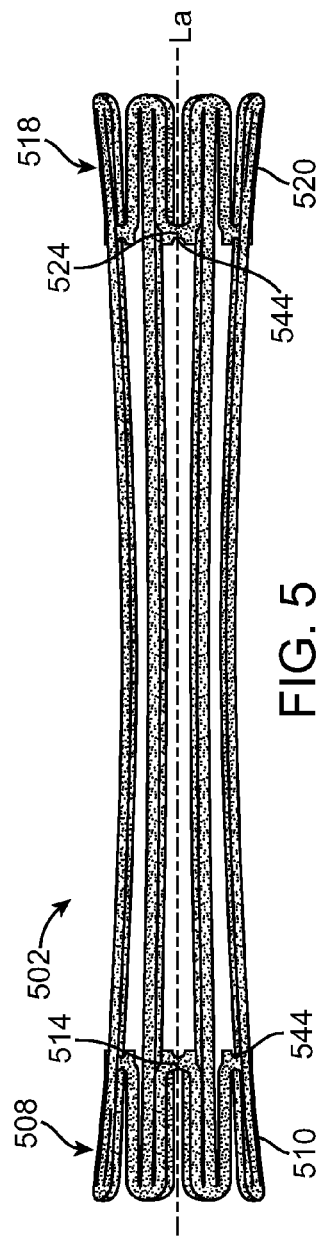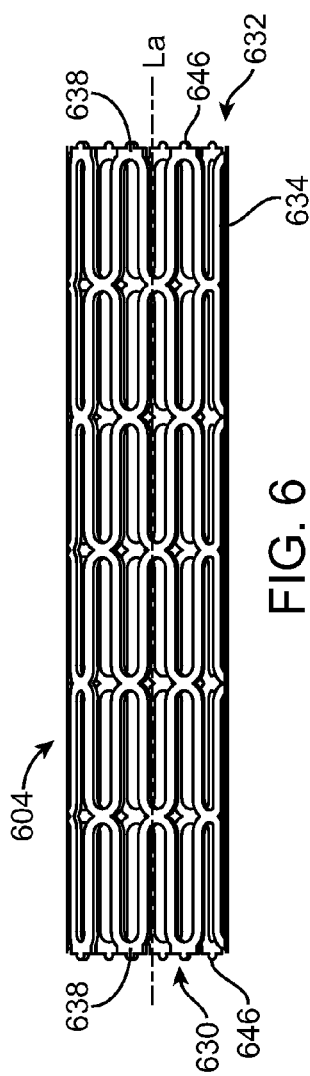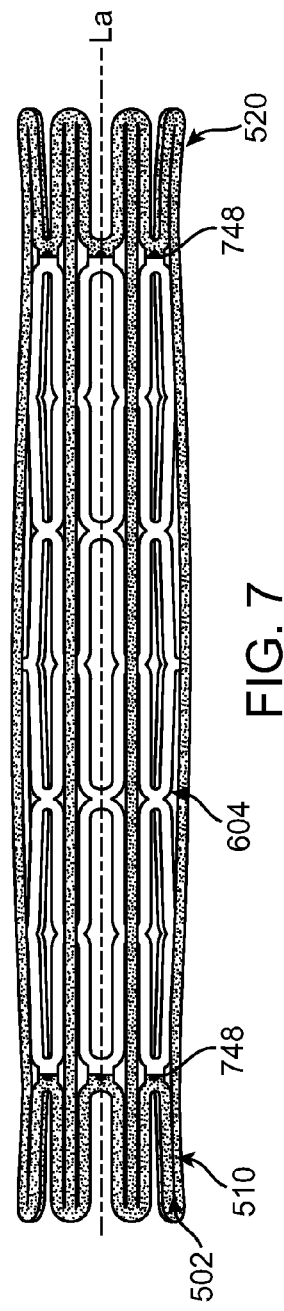

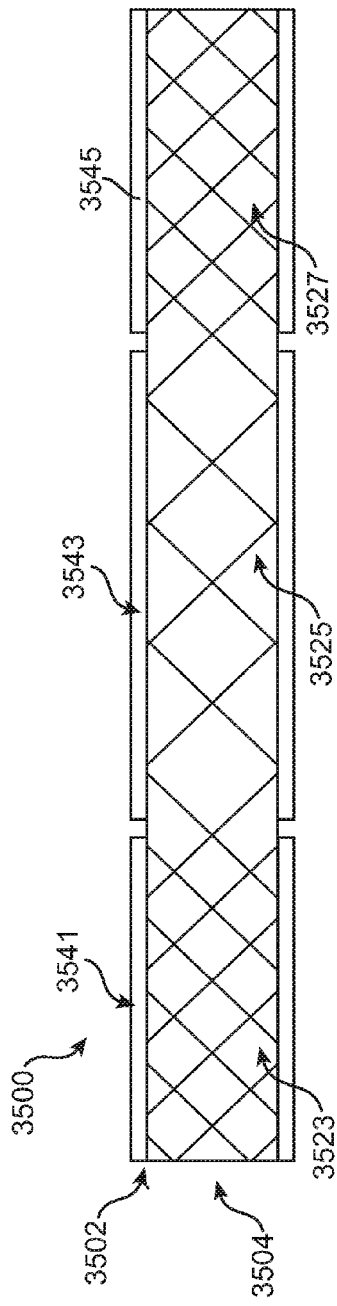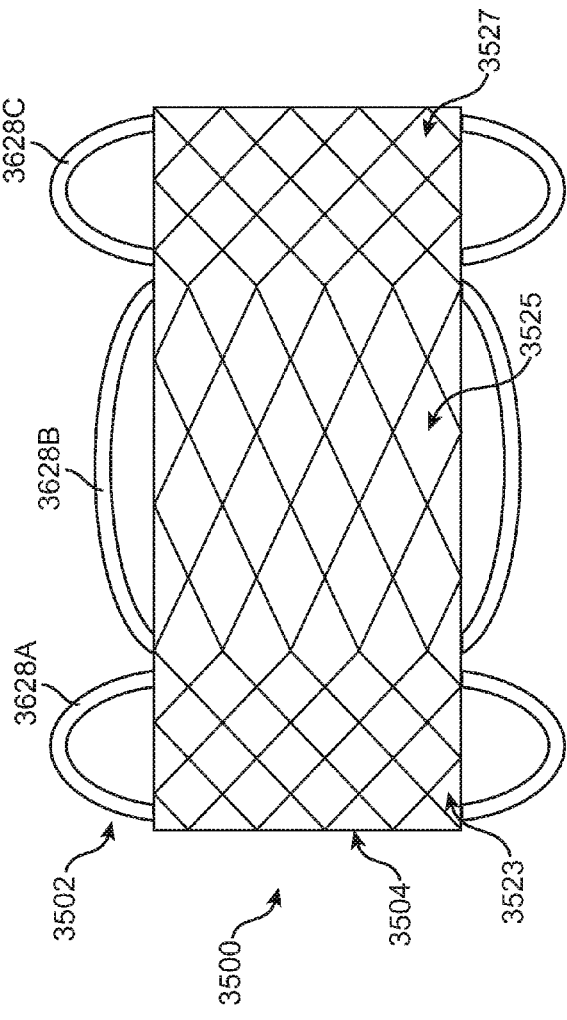

DOUBLE-WALLED STENT SYSTEM

FIELD OF THE INVENTION

The present invention is directed to intraluminal stents for use in a body lumen. More particularly, the present invention is directed to a double-walled stent system.

BACKGROUND OF THE INVENTION

Heart valves, such as the mitral, tricuspid, aortic and pulmonary valves, are sometimes damaged by disease or by aging, resulting in problems with the proper functioning of the valve. Heart valve problems generally take one of two forms: stenosis, in which a valve does not open completely or the opening is too small, resulting in restricted blood flow; or insufficiency, in which blood leaks backward across a valve when it should be closed.

The pulmonary valve regulates blood flow between the right ventricle and the pulmonary artery, controlling blood flow between the heart and the lungs. Pulmonary valve stenosis is frequently due to a narrowing of the pulmonary valve or the pulmonary artery distal to the valve. This narrowing causes the right side of the heart to exert more pressure to provide sufficient flow to the lungs. Over time, the right ventricle enlarges, which leads to congestive heart failure (CHF). In severe cases, the CHF results in clinical symptoms including shortness of breath, fatigue, chest pain, fainting, heart murmur, and in babies, poor weight gain. Pulmonary valve stenosis most commonly results from a congenital defect, and is present at birth, but is also associated with rheumatic fever, endocarditis, and other conditions that cause damage to or scarring of the pulmonary valve. Valve replacement may be required in severe cases to restore cardiac function.

Previously, valve repair or replacement required open-heart surgery with its attendant risks, expense, and extended recovery time. Open-heart surgery also requires cardiopulmonary bypass with risk of thrombosis, stroke, and infarction. To address the need for pulmonary valve replacement, various implantable pulmonary valve prostheses, delivery devices and surgical techniques have been developed and are presently in use. One such prosthesis is a bioprosthetic, valved conduit having a glutaraldehyde treated bovine jugular vein containing a natural, trileaflet venous valve, and a sinus. A similar device is composed of a porcine aortic valve sutured into the center of a woven fabric conduit. A common conduit used in valve replacement procedures is a homograft, which is a vessel harvested from a cadaver. Valve replacement using either of these devices requires thoracotomy and cardiopulmonary bypass.

As previously mentioned, pulmonary valve stenosis most commonly occurs in infants and young children when the condition results from a congenital defect. Frequently, the pulmonary valve must be replaced with a prosthetic valve when the child is young, usually less than five years of age. However, as the child grows, the valve can become too small to accommodate the blood flow to the lungs that is needed to meet the increasing energy demands of the growing child, and it may then need to be replaced with a larger valve. Alternatively, in a patient of any age, the implanted valve may fail to function properly over time due to calcium buildup and have to be replaced. In either case, repeated surgical or transvenous procedures are required.

When the valve in the prostheses must be replaced, for the reasons described above or other reasons, an additional surgery is required. Because many patients undergo their first procedure at a very young age, they often undergo numerous procedures by the time they reach adulthood. These surgical replacement procedures are physically and emotionally taxing, and a number of patients choose to forgo further procedures after they are old enough to make their own medical decisions.

Recently, flexible stented valve prostheses and various delivery devices have been developed so that replacement valves can be delivered transvenously using a catheter-based delivery system. These stented valves include a collapsible valve attached to the interior of a tubular frame or stent. The valve can be any of the valve prostheses described above, or it can be any other suitable valve. The stented valves can also include a tubular portion or "stent graft" that can be attached to the interior or exterior of the stent to provide a generally tubular internal passage for the flow of blood when the leaflets are open. The graft can be separate from the valve and it can be made from any suitable biocompatible material including, but not limited to, fabric, a homograft, porcine vessels, bovine vessels, and equine vessels. The stent portion of the device can be reduced in diameter, mounted on a catheter, and advanced through the circulatory system of the patient. The stent portion can be either self-expanding or balloon expandable. In either case, the stented valve can be positioned at the delivery site, where the stent portion is expanded against the wall of a previously implanted prostheses or a native vessel to hold the valve firmly in place. The valve survives the compression and subsequent expansion in fully working form. One embodiment of a stented valve is disclosed in U.S. Pat. No. 5,957,949 to Leonhardt et al. entitled "Percutaneous Placement Valve Stent", which is incorporated by reference herein in its entirety. Although the valve may later require replacement, the patient may receive multiple replacement valves using the minimally invasive catheter method rather than requiring further invasive surgery.

It is an object of the present invention to disclose a stent system for treating anomalies and/or growth of the right ventricular outflow tract. The stent system can be delivered transvenously using a catheter-based delivery system.

BRIEF SUMMARY OF THE INVENTION

Embodiments of the present invention relate to a stent system for use within a body lumen. The stent system includes an interior stent component having a proximal end, a distal end, and a generally tubular cylindrical body defining a central flow lumen there through. The stent system also includes an exterior stent component including a plurality of longitudinally-extending connectors, wherein the proximal and distal ends of the interior stent component are attached to the exterior stent component such that the longitudinally-extending connectors are radially positioned around the tubular body of the interior stent component. When the stent system is in an expanded configuration, the longitudinally-extending connectors of the exterior stent component are configured to bow radially outward against a vessel wall of the body lumen while the interior stent component remains radially positioned within the longitudinally-extending connectors.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 2A is an enlarged planar view of a portion of an exterior stent component according to another embodiment of the present invention.

FIG. 2B is an enlarged planar view of a portion of an exterior stent component according to another embodiment of the present invention.

FIG. 5 is a side view of an exterior stent component according to another embodiment of the present invention.

FIG. 6 is a side view of an interior stent component according to another embodiment of the present invention.

FIG. 7 is a side view of the stent system having an exterior stent component and an interior stent component joined together by a snap-fit connection according to another embodiment of the present invention.

FIG. 35 is a side view of a segmented double walled stent system according to an embodiment of the present invention, wherein the system is in a contracted or compressed configuration.

FIG. 36 is a side view of a segmented double walled stent system of FIG. 35, wherein the system is in a contracted or compressed configuration.

DETAILED DESCRIPTION OF THE INVENTION

Figure 1:
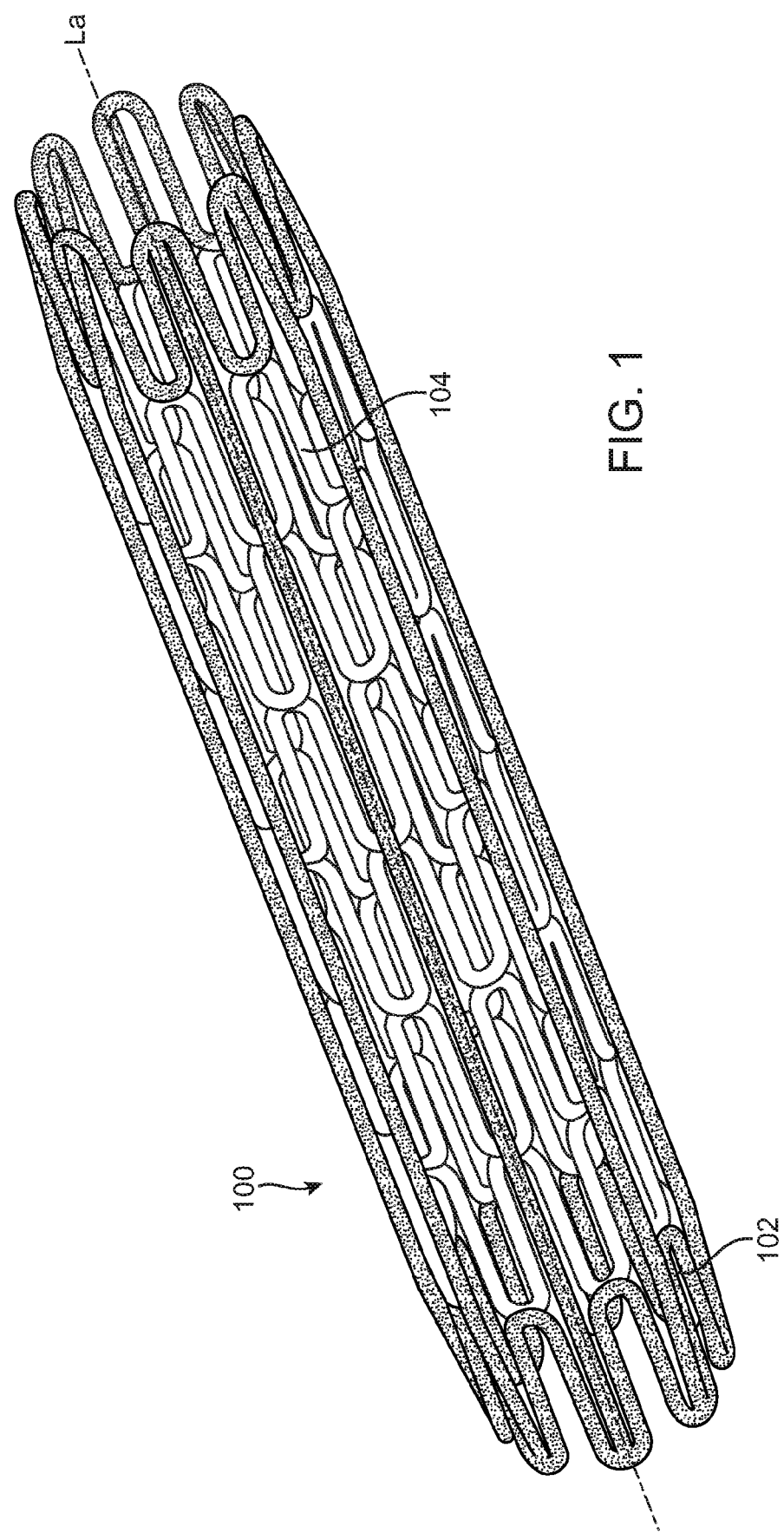
FIG. 1 is a perspective view of a double walled stent system having an exterior stent component and an interior stent component according to an embodiment of the present invention.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as the coronary, carotid and renal arteries, the invention may also be used in any other body passageways where it is deemed useful. Furthermore, there is no intention to be bound by any expressed or implied theory presented in the preceding technical field, background, brief summary or the following detailed description.

Embodiments of the present invention relate to a double walled stent system having two stent components, an exterior stent component and an interior stent component. The double walled stent system has a contracted or compressed configuration sufficient for delivery to the treatment site, and an expanded or deployed configuration for contacting the vessel wall. When deployed, the exterior stent component comes in contact with the vessel wall and aids in fixing the stent system to the treatment site. In addition, the exterior stent component provides scaffolding to support the vessel wall. The interior stent component also expands but remains centered inside the exterior component. The interior stent component is radially centered inside the lumen of the vessel, or is located mid-lumen, and makes little to no contact with the vessel wall. A surface of the interior stent component may be covered with material, such as a graft, such that the interior stent component defines a central flow lumen for directing blood flow through the center of the stent system. When properly implanted within the vessel, blood flow is directed through the central flow lumen defined by the interior stent component without traveling to the outer walls of the exterior stent component. The interior stent component thus provides the stent system with a consistent central flow lumen of predetermined expanded diameter, such as a diameter consistent with the normal diameter of the body vessel in which it is to be implanted, to accommodate blood flow there through. In addition, the central flow lumen of the interior stent component accommodates the placement of a secondary device, such as a valve. Concurrently, the exterior stent component provides the stent system with a larger outer diameter, which in some embodiments may also be variable, to conform to and provide opposition forces against a vessel wall.

A separation between the central flow lumen defined by an inner surface of the interior stent component and the outer diameter defined by an outer surface of the exterior stent component allows for the placement of a secondary device having a fixed-diameter, such as a valve, into a vessel of relatively larger size and/or irregular shape. More particularly, the double walled construction of the stent system provides a certain amount of mechanical isolation between an inner wall of the stent system defined by the interior stent component and an outer wall of the stent system defined by the exterior stent component. Mechanical isolation as used herein is intended to describe that the outer wall of the stent system minimizes or isolates the inner wall of the stent system from mechanical forces applied to the stent system from the vessel wall, thus reducing the possibility that the central flow lumen of the stent system defined by the interior stent component will be distorted in shape or size. The exterior stent component conforms to and provides the required wall opposition forces against a vessel wall of a relatively larger and/or irregularly shape vessel. The interior stent component is protected or isolated from the vessel wall, and thus may hold a secondary device having a fixed diameter, such as a valve. The ability to deploy the double walled stent system into an irregular shaped vessel and assure that the central flow lumen remains a uniform diameter consistent with the vessel dimensions proximal and distal to the implantation site is important to direct blood flow through the stent system and, if applicable, assure proper valve placement. For example, it may be desirable for the interior stent component to include a valve therein to regulate flow there through, such as when the double walled stent system is utilized in the right ventricular outflow tract. When a valve is utilized within the interior stent component, it is required that the interior stent component act as a blood flow conduit for directing blood flow through the center of the device and restricting blood flow from the outer walls of the stent system. The double walled stent system is particularly suited for treating the right ventricular outflow tract because the exterior stent component allows for patient growth and/or adjusts to anomalies of a body lumen such that fewer replacement surgeries are required. In addition to addressing anomalies of the right ventricular outflow tract, the double walled stent system may be used to address other vascular defects that require space filling apposition while maintaining a central flow lumen, e.g., vessel dilatation, aneurysm, or other vascular congenital defects with similar morphologies. Further details and description of the embodiments of the present invention are provided below with reference to FIGS. 1-40A.

Figure 33:
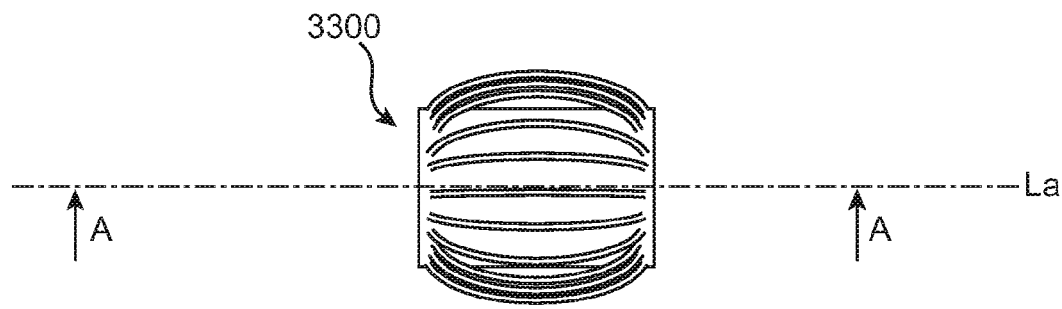
FIG. 33 is a side view of a double walled stent system in an expanded configuration according to an embodiment of the present invention.
Figure 33A:
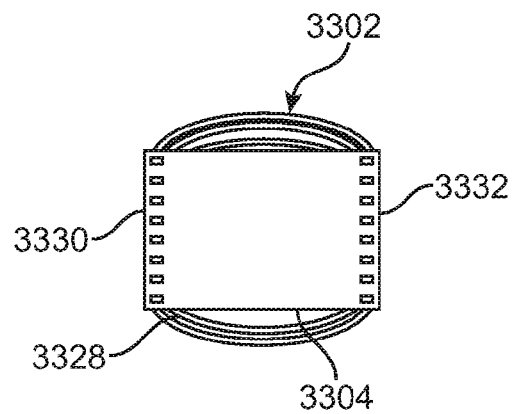
FIG. 33A is a sectional view of the double walled stent system of FIG. 33 taken along line A-A of FIG. 33.
Figure 34:
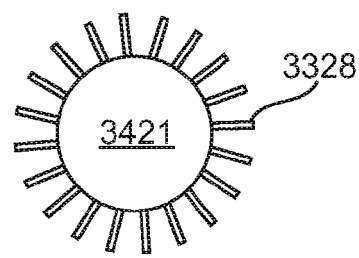
FIG. 34 is an end view of the double walled stent system of FIG. 33 in an expanded configuration.

FIGS. 33, 33A, and 34 illustrate an embodiment of a double walled stent system 3300. Stent system 3300 includes two stent components, an exterior stent component 3302 and an interior stent component 3304, one of which overlays the other to form a generally cylindrical body having a common longitudinal axis $L_a$. Exterior stent component 3302 includes an outer surface that defines an outer diameter of stent system 3300, while interior stent component 3304 defines a central flow lumen 3421 there through with an inner diameter of stent system 3300. The central flow lumen 3421 has a consistent predetermined expanded diameter to accommodate blood flow there through. For example, the consistent predetermined expanded diameter may be approximately the same as the normal diameter of the body vessel in which the stent system is to be implanted. Interior stent component 3304 has a cylindrically-shaped tubular body that extends between a proximal end 3330 and a distal end 3332. Interior stent component 3304 may be any appropriate stent configuration known to one of skill in the art and may include a valve (not shown) located therein.

Exterior stent component 3302 includes a plurality of longitudinally-extending bands or spars 3328. Bands 3328 are generally straight strips or planks of material extending parallel to common longitudinal axis $L_a$ from proximal end 3330 to distal end 3332 of interior stent component 3304. More particularly, the proximal end of each longitudinally-extending band 3328 is connected proximate proximal end 3330 of interior stent component 3304, and the distal end of each longitudinally-extending band 3328 is connected proximate distal end 3332 of interior stent component 104. Bands 3328 have a length approximately equal to the length of the tubular body of interior stent component 3304. Interior stent component 3304 is radially centered inside of or within bands 3328 of exterior stent component 3302, and attached thereto by welding or by any other appropriate mechanical method for connecting exterior stent component 3302 and interior stent component 3304.

Longitudinally-extending bands 3328 of exterior stent component 3302 are deployed or radially expanded via foreshortening dynamics of the interior stent component 3304. More specifically, interior stent component 3304 is designed to have a specific amount of foreshortening or contraction which reduces the length of the interior stent component upon radial expansion. Thus upon radial expansion of stent system 3300, interior stent component 3304 increases in diameter and decreases in length, causing bands 3328 to bulge or bow outwards towards the vessel wall. Since the proximal and distal ends of bands 3328 move closer together upon the foreshortening of the interior stent component 3304, deployed bands 3328 of exterior stent component 3302 bow radially outward to come in contact with the vessel wall and aid in fixing stent system 3300 to the treatment site. Interior stent component 3304 radially expands such that central flow lumen 3421 reaches an expanded diameter, but an outer surface of interior stent component 3304 makes little to no contact with the vessel wall but rather remains radially centered inside exterior stent component 3302. Interior stent component 3304 is configured so that central flow lumen 3421 is of a substantially consistent diameter with the vessel dimension proximal and distal of the implanted stent system 3300.

In another embodiment of the present invention, the double-walled stent system may include multiple segments, or distinct portions or zones so that the exterior stent component may provide the stent system with a variable larger outer diameter to conform to and provide opposition forces against a vessel wall. For example, double walled stent system 3500 shown in FIG. 35 includes an exterior stent component 3502 having three distinct segments 3541, 3543, and 3545 that each include a plurality of independent longitudinally-extending bands. Segments 3541, 3543, and 3545 are separately attached to an interior stent component 3504 having three corresponding distinct portions, i.e., a proximal portion 3523, an intermediate portion 3525, and a distal portion 3527. Outer surfaces of segments 3541, 3543 and 3545 define an outer diameter of stent system 3500, which upon expansion may vary from segment to segment. The cylindrically-shaped tubular body of interior stent component 3504, which includes proximal portion 3523, intermediate portion 3525, and distal portion 3527, defines a central flow lumen (not shown) there through that provides an inner diameter of stent system 3500. Each portion 3523, 3525, and 3527 of interior stent component 3504 may be designed to shorten upon expansion by a same or different amount or, otherwise stated, have greater, lesser or equal foreshortening ratios based on strut design than any other portion. In various embodiments, exterior stent component 3502 and interior stent component 3504 can have any number of corresponding segments or portions depending upon the desired operation of stent system 3500.

Each segment 3541, 3543 and 3545 of exterior stent component 3502 includes a plurality of longitudinally-extending bands or spars that are generally straight strips or planks of material extending from a proximal end to a distal end of a corresponding portion 3523, 3525, and 3527, respectively, of interior stent component 3504. More particularly, a plurality of independent longitudinally-extending bands 3628A that make-up segment 3541 are radially located around proximal portion 3523 of interior stent component 3504. The proximal end of each longitudinally-extending band 3628A is connected to a proximal end of proximal portion 3523, and the distal end of each longitudinally-extending band 3628A is connected to a distal end of proximal portion 3523. Similarly, a plurality of independent longitudinally-extending bands 3628B that make-up segment 3543 are radially located around intermediate portion 3525 of interior stent component 3504. The proximal end of each longitudinally-extending band 3628B is connected to a proximal end of intermediate portion 3525, and the distal end of each longitudinally-extending band 3628B is connected to a distal end of intermediate portion 3525. Further, a plurality of longitudinally-extending bands 3628C that make-up segment 3545 are radially located around distal portion 3527 of interior stent component 3504. The proximal end of each longitudinally-extending band 3628C is connected to a proximal end of distal portion 3527, and the distal end of each longitudinally-extending band 3628C is connected to a distal end of distal portion 3527.

In the embodiment illustrated in FIGS. 35-36, intermediate portion 3525 of interior stent component 3504 is has a strut design that has less relative foreshortening upon expansion than proximal and distal portions 3523, 3527. The difference in the amount of foreshortening between portions 3523, 3525 and 3527 results in a difference in the height of expansion of segments 3541, 3543 and 3545 of exterior stent component 3502. More particularly, the segments 3541, 3543 and 3545 of exterior stent component 3502 are deployed or radially expanded via foreshortening dynamics of the corresponding portion of interior stent component 3504. Due to the greater relative amount of foreshortening experienced by proximal and distal portions 3523, 3527 of interior stent component 3504, segments 3541, 3545 of exterior stent component 3502 expand or bow radially outward more than segment 3543 connected to corresponding intermediate section 3525. The number of segments and stent portions with various foreshortening ratios may be selected for the intended anatomy and dimensions of a target implant area such that the differential expansion heights of the segments may be customized to provide minimum force in thin areas of the vessel wall while providing maximum opposing forces where the vessel wall can sustain greater forces.

Referring to FIG. 1, a perspective view of a double walled stent system 100 according to another embodiment of the present invention is shown. Stent system 100 includes two stent components, an exterior stent component 102 and an interior stent component 104. Interior stent component 104 has a generally tubular cylindrical body having a plurality of stent struts connected together and is centered inside of or within exterior stent component 102. Exterior stent component 102 and interior stent component 104 are manufactured as independent detached components that may be connected to each other via soldering, welding or other attachment means. Exterior stent component 102 and interior stent component 104 are aligned on a common longitudinal axis $L_a$ to form a generally cylindrical body having radial and longitudinal axes.

Figure 2:
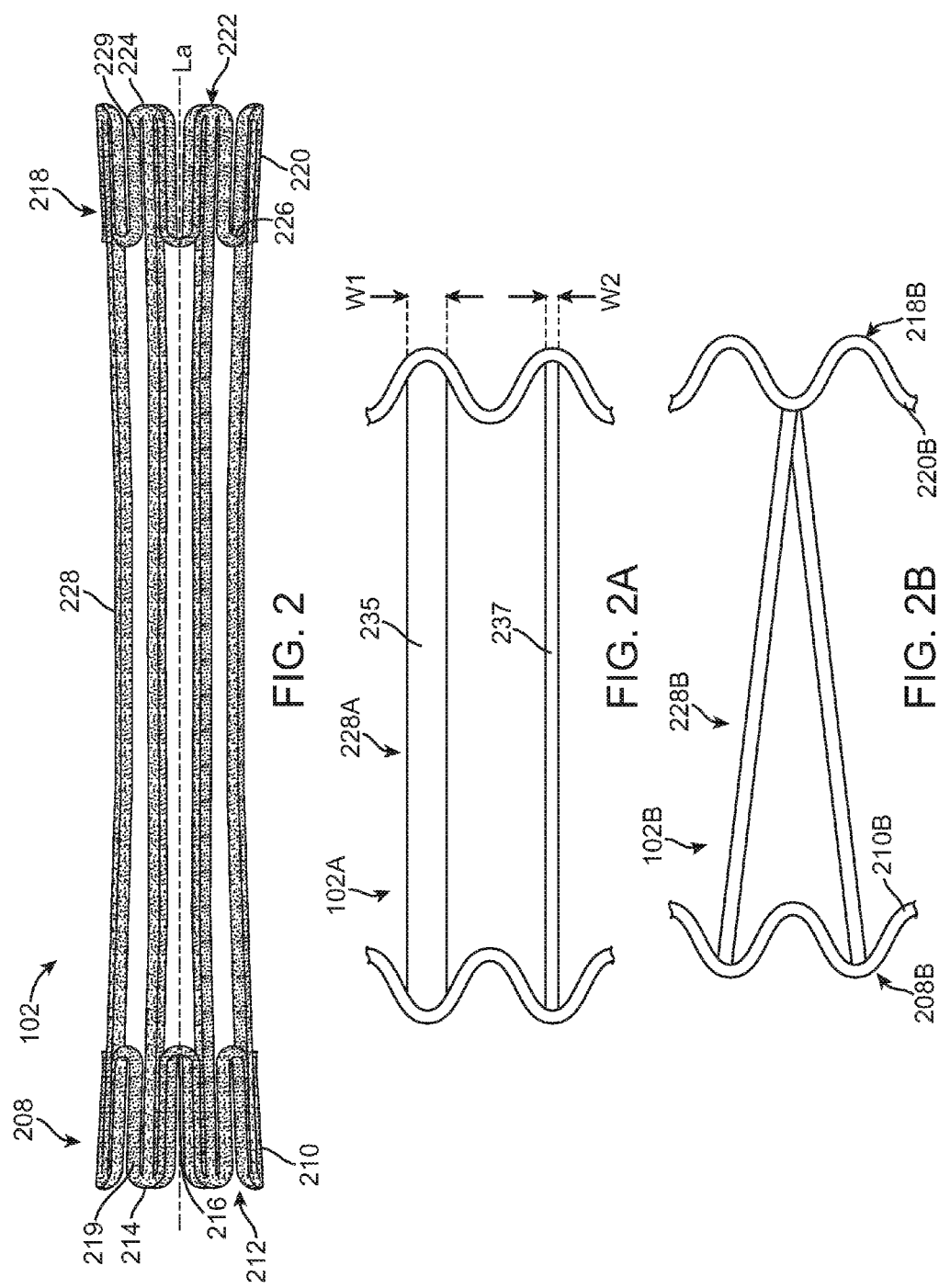
FIG. 2 is a side view of an exterior stent component according to an embodiment of the present invention.

With reference to FIG. 2, exterior stent component 102 has a proximal portion 208 and a distal portion 218. Proximal portion 208 includes a generally cylindrical stent strut 210, and distal portion 218 includes a generally cylindrical stent strut 220. Proximal and distal stent struts 210, 220 are aligned on common longitudinal axis $L_a$ and are connected by a plurality of longitudinally-extending connectors such as straight bands 228. Longitudinal axis $L_a$ extends within the cylindrical body from a proximal end 212 to a distal end 222 of exterior stent component 102. Straight bands 228 are generally straight strips or planks of material extending parallel to common longitudinal axis $L_a$ from proximal portion 208 to distal portion 218 of exterior stent component 102 in order to connect proximal and distal stent struts 210, 220. In the embodiment depicted in FIG. 2, straight bands 228 each have approximately the same width.

In another embodiment of the present invention, the width of a first longitudinally-extending connector may be different from the width of a second longitudinally-extending connector. For example, FIG. 2A illustrates an expanded planar view of a portion of an exterior stent component 102A including a plurality of longitudinally-extending connectors 228A. A first band 235 has a width of W1 and a second band 237 has a width of W2, wherein W1 is greater than W2. Constructing the longitudinally-extending connectors of different widths may increase fixation of the stent system within the vessel wall, and allow for the matching of longitudinally-extending connectors with variable widths to vessel wall constraints. By altering the surface area of the longitudinally-extending connectors, the forces are dissipated over a larger footprint resulting in less vessel wall damage and greater fixation. For example, a device having longitudinally-extending connectors with an assortment of widths around the circumference of the device provides the option of having the device placed in a vessel at a particular orientation. This would be of particular advantage in a vessel with both thin and thick wall thicknesses since the device may be oriented in the vessel to minimize damage to a thin wall area.

Referring back to FIG. 2, stent strut 210 at proximal portion 208 of exterior stent component 102 is a wavelike or sinusoidal cylindrical band or ring having a pattern of straight segments 219 with crowns 214 connecting adjacent straight segments 219. For purposes of this application, it will be understood that crowns are the concave turns or curves of a wavelike or sinusoidal band. Straight segments 219 and crowns 214 of stent strut 210 are not necessarily coupled together at the ends, but instead flow or continue one into another. Other embodiments may be manufactured differently, such that some portions may be mechanically coupled together via welding, soldering, adhesive or another bonding or another mechanical connection method. However, to describe the particular structure of stent strut 210, various segments and crowns may be described as being connected or coupled to each other. Thus, the terms "connect with," "connected," or "coupled" may mean either integrally continuing or flowing together or mechanically coupled together. Similar to stent strut 210, stent strut 220 at distal portion 218 of exterior stent component 102 is a wavelike or sinusoidal cylindrical band or ring having a pattern of straight segments 229 and crowns 224 connecting adjacent straight segments 229. In one embodiment, stent struts 210, 220 include eight crowns each but it will be apparent to those of ordinary skill in the art that the number of crowns may vary.

As previously mentioned, straight bands 228 are generally straight strips or planks of material extending parallel to common longitudinal axis $L_a$ from proximal end 212 to distal end 222 of exterior stent component 102. More particularly, the proximal end of each longitudinally-extending straight band 228 is connected to a valley 216 of crown 214 of stent strut 210, and the distal end of each straight band 228 is connected to an opposing valley 226 of crown 224 of stent strut 220. For purposes of this application, it will be understood that valleys are the open curved or hollowed out portion formed by the crowns of a wavelike or sinusoidal band. Since the longitudinally-extending connectors extend from a valley of the proximal stent strut to a valley of the distal stent strut, they may be referred to as "valley-to-valley" connectors. As valley-to-valley connectors, straight bands 228 have a length approximately equal to the lengths of the stent struts 210, 220 in addition to the length of interior stent component 104 such that interior stent component 104 may be centered between stent struts 210, 220. In one embodiment, exterior stent component 102 includes a total of eight longitudinally-extending straight bands 228.

In another embodiment of the present invention, the longitudinally-extending connectors are not parallel to common longitudinal axis $L_a$. For example, FIG. 2B illustrates an enlarged planar view of a portion of an exterior stent component 102B including a plurality of longitudinally-extending connectors 228B. Connectors 228B are strips or planks of material that connect proximal portion 208B to distal portion 218B of exterior stent component 102B in order to connect proximal and distal stent struts 210B, 220B. Connectors 228B do not extend parallel to common longitudinal axis $L_a$ but rather are slanted or angled with respect to common longitudinal axis $L_a$. More particularly, the proximal ends of each connector 228B are spaced apart and are connected within adjacent valleys of stent strut 210B, whereas the distal ends of each connector 228B overlap and are connected to a single crown of stent strut 220B. The slant or angle of connectors 228B may aid in stabilizing expanded connectors 228B, thereby exerting additional force onto the vessel wall to aid in fixing the stent system to the treatment site.

Figure 3:
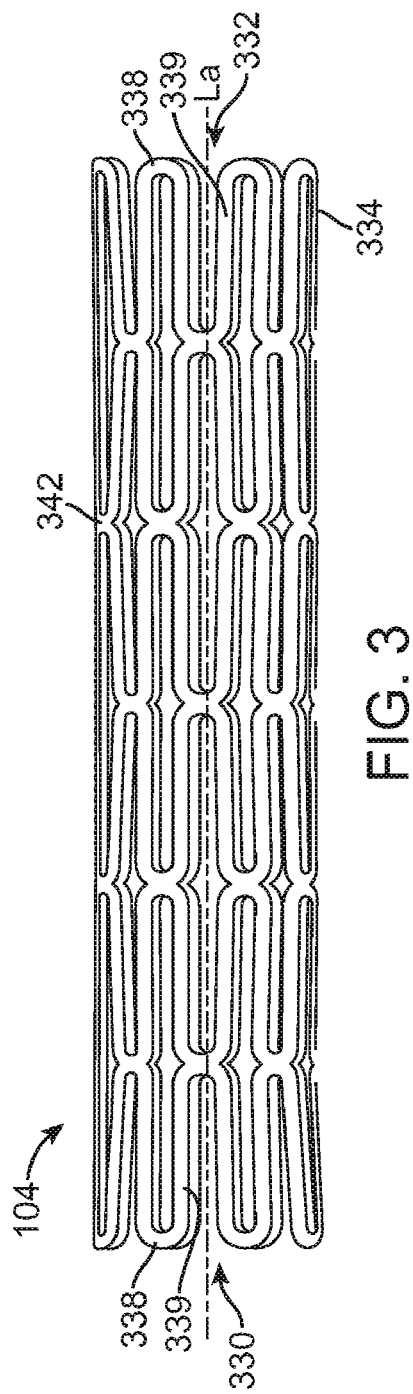
FIG. 3 is a side view of an interior stent component according to an embodiment of the present invention.

Referring now to FIG. 3, interior stent component 104 is a cylindrically-shaped tubular body having common longitudinal axis $L_a$, a proximal end 330, and a distal end 332. Longitudinal axis $L_a$ extends within the cylindrical body from proximal end 330 to distal end 332 of interior stent component 104. A plurality of adjacent stent struts 334 are aligned substantially parallel relative to longitudinal axis $L_a$ so as to form the cylindrically-shaped tubular body shape of interior stent component 104. FIG. 3 shows interior stent component 104 having six stent struts 334 connected at connections 342. One of ordinary skill in the art will appreciate that interior stent component 104 can have any number of stent struts 334 depending upon the desired length of stent system 100.

Each stent strut 334 is a wavelike or sinusoidal cylindrical band or ring having a pattern of straight segments 339 and crowns 338 connecting adjacent straight segments 339. For purposes of this application, it will be understood that crowns are the concave turns or curves of a wavelike or sinusoidal band. Straight segments 339 and crowns 338 of each wavelike or sinusoidal cylindrical band are not necessarily coupled together at the ends, but may continue or flow one into another. Each stent strut 334 is functionally the same in that they each include a substantially similar pattern of straight segments 339 and crowns 338. Adjacent stent struts 334 are aligned such that a crown of one strut is aligned with a corresponding crown of an adjacent stent strut 334. Connections 342 between adjacent stent struts 334 are formed where crowns of adjacent stent struts 334 are aligned. Connections 342 are preferably formed by welding the turns together, such as by resistance welding, friction welding, laser welding or another form of welding such that no additional materials are used to connect stent struts 334. Alternatively, stent struts 334 can be connected by soldering, by the addition of a connecting element between the turns, or by another mechanical method. Further, interior stent component 104 may be formed pre-connected as a unitary structure, such as by laser cutting or etching the entire stent body from a hollow tube or sheet. Other connections or ways to join adjacent struts would be apparent to one skilled in the art and are included herein. Interior stent component 104 may be any appropriate stent known in the art and may include a valve located therein as will be explained in more detail below.

Figure 4:
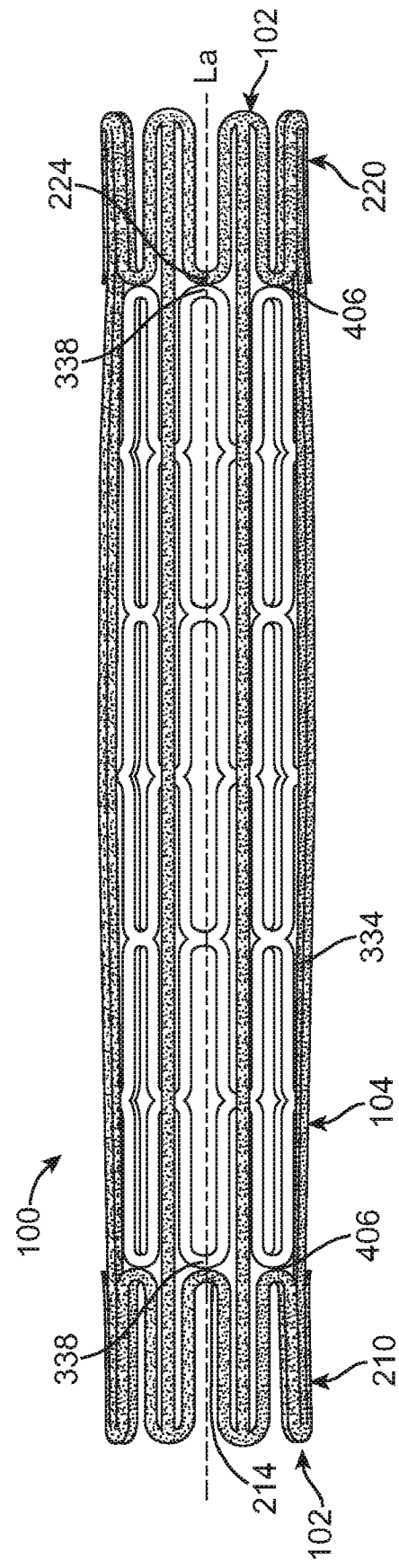
FIG. 4 is a side view of the stent system having an exterior stent component and an interior stent component joined together according to an embodiment of the present invention.

FIG. 4 illustrates exterior stent component 102 and interior stent component 104 joined together at connections 406 to form double walled stent system 100. Interior stent component 104 is centered between struts 210, 220 of exterior stent component 102. Exterior and interior stent components 102, 104 are aligned such that outermost crowns 338 at the proximal and distal ends of interior stent component 104 are aligned with the innermost crowns 214, 224 of proximal and distal stent struts 210, 220, respectively, of exterior stent component 102. Connections 406 are formed where adjacent outermost and innermost crowns are aligned. Connections 406 are preferably formed by welding the turns together, such as by resistance welding, friction welding, laser welding or another form of welding such that no additional materials are used to connect exterior stent component 102 and interior stent component 104. Alternatively, exterior stent component 102 and interior stent component 104 can be connected by soldering, by the addition of a connecting element between the turns, or by another mechanical method. In the embodiment shown in FIG. 4, interior stent component 104 includes six stent struts 334, such that when interior stent component 104 is connected or fused to exterior stent component 102 to form stent system 100, stent system 100 has eight stent struts or segments total.

In another embodiment described with reference to FIGS. 5-10, exterior stent component 102 and interior stent component 104 may be configured to include a snap-fit or interference connection there between. The snap-fit connection is a mechanical interlock having a male component of the interior stent component received within a corresponding female component of the exterior stent component. The male and female components of the snap-fit connection are joined by press fit, and are further fused together via welding, soldering, or cryogenically coupling. The snap-fit connection assures proper alignment of the exterior and interior stent components. In addition, the welded snap-fit connection does not increase the outer diameter of the stent system, thus minimizing overall dimensions of the stent system, and minimizes or mitigates the stresses compared to other weld configurations.

With reference to FIG. 5, exterior stent component 502 is configured to be connected to a corresponding interior stent component by the inclusion of female receptacles 544 located at both a proximal portion 508 and a distal portion 518 of exterior stent component 502. Female receptacles 544 are located on the innermost crowns 514, 524 of stent struts 510, 520, respectively. As shown in FIG. 6, interior stent component 604 is configured to be connected to exterior stent component 502 by the inclusion of male tabs 646 located at both a proximal end 630 and a distal end 632 of interior stent component 604. Male tabs 646 are located at the outermost crowns 638 of the most proximal stent strut 634, as well as at the outermost crowns 638 of the most distal stent strut 634. Male tabs 646 are configured to fit within female receptacles 644 of exterior stent component 502. FIG. 7 illustrates a stent system 700 including exterior stent component 502 and interior stent component 604 joined together via snap-fit connections 748. Interior stent component 604 is centered between struts 510, 520 of exterior stent component 502. Exterior and interior stent components 502, 604 are aligned such that male tabs 646 of interior stent component 604 are received within female receptacles 544 of exterior stent component 502. Male tabs 646 are press fit within female receptacles 544, and snap-fit connection 748 is further welded, soldered, or cryogenically coupled. A cryogenically coupled snap-fit connection 748 avoids the metallurgical effects and technical difficulties of welding or fusing NiTi (Nitinol) to a dissimilar metal, such as, for example, CoCr alloys, stainless steels, MP35N alloys. In addition, there are some manufacturability advantages to a cryogenically coupled snap-fit connection 748 such as avoiding welding and the resulting heat introduction that could affect components formed of tissue such as a porcine valve or homograft material, polymeric agents, or pharmacological agents present on a component of the stent system.

Figure 8:
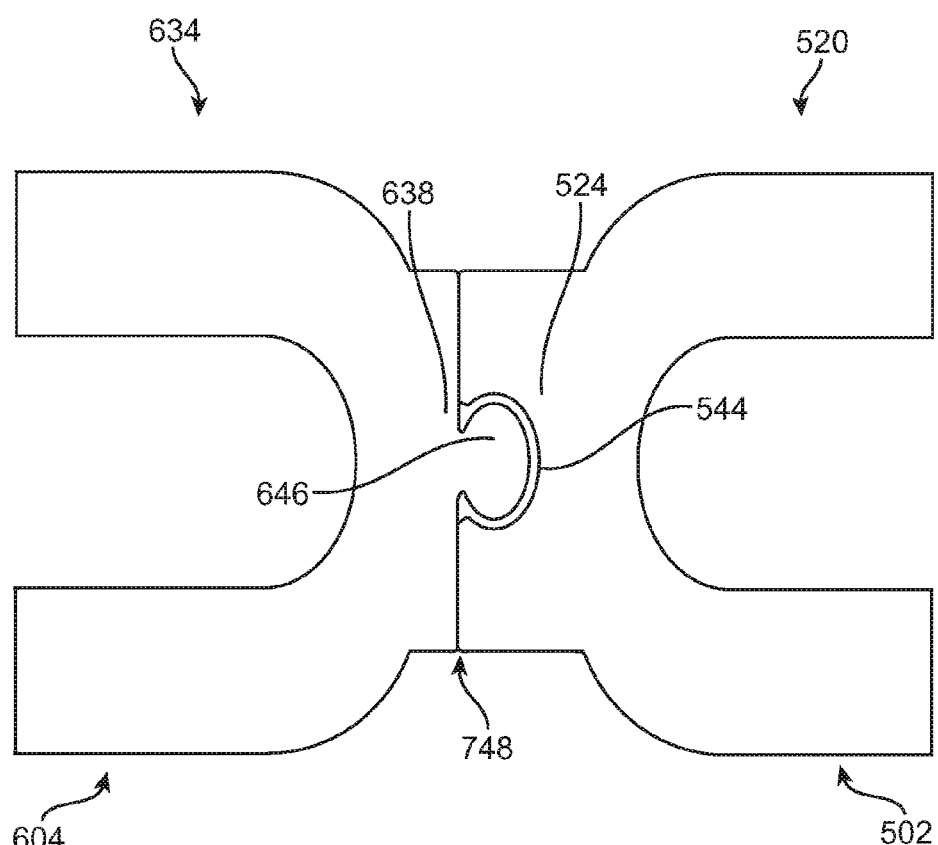
FIG. 8 is an enlarged planar view of the snap-fit connection of FIG. 4.

FIG. 8 illustrates an enlarged planar view of a snap-fit connection 748 between stent strut 634 of interior stent component 604 and stent strut 520 of exterior stent component 502. Each snap-fit connection 748 is a mechanical interlock that includes a male component (male tab 646) extending from an outermost crown 638 of the interior stent component's most distal stent strut 634 and a female component (female receptacle 544) extending within an innermost crown 524 of stent strut 520. Each male component is thus received within a corresponding female component. In the embodiment depicted in FIG. 8, male tab 646 has planar upper and lower surfaces and a substantially rounded perimeter with female receptacle 544 being a corresponding substantially circular recess. The male and female components of snap-fit connection 748 with the attached strut sections are separately formed requiring assembly thereof. The male and female components of snap-fit connection 748 may be joined by a press fit, and further fused together via welding, soldering, or cryogenically coupling. The snap-fit connection assures proper alignment of the exterior and interior stent components and minimizes or mitigates the stresses compared to other weld configuration. Although snap-fit connection 748 is illustrates with a male component (male tab 646) located on interior stent component 604 and a female component (female receptacle 544) located on exterior stent component 502, it should be understood by those of ordinary skill in the art that the male component may instead by located on the exterior stent component and the female component may be located on the interior stent component.

Figure 9:
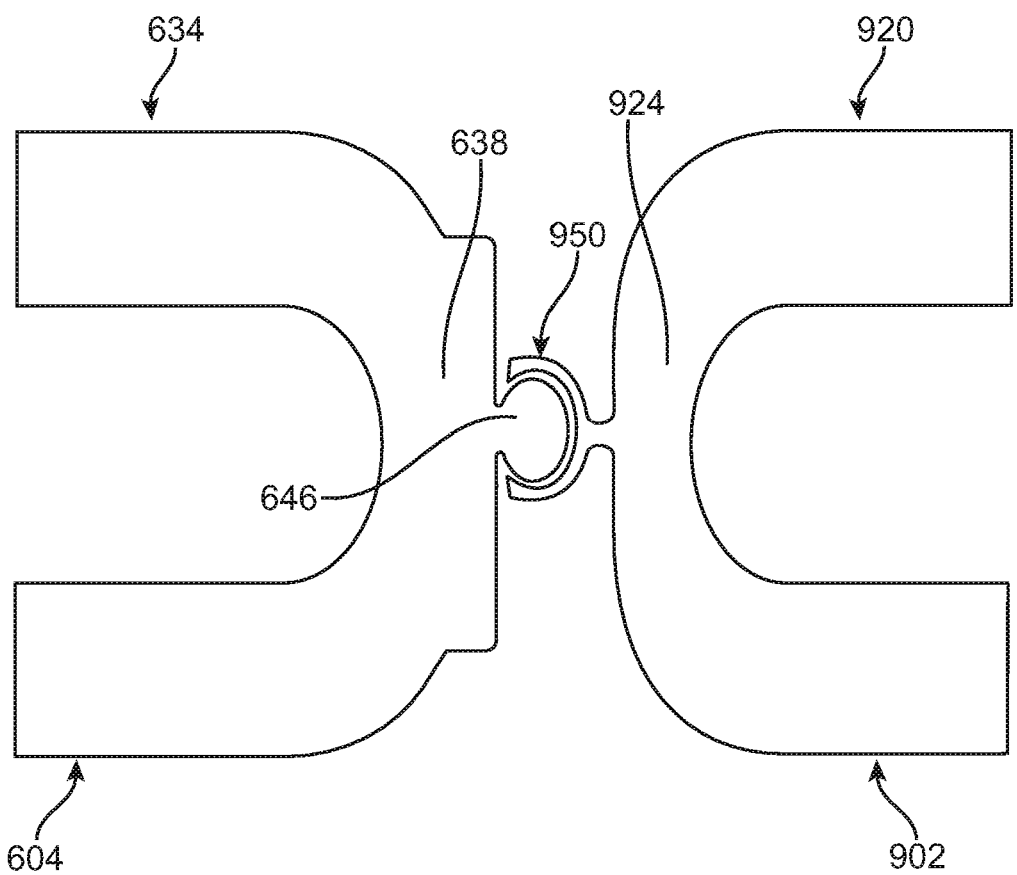
FIG. 9 is an enlarged planar view of another embodiment of a snap-fit connection between an exterior stent component and an interior stent component.

FIG. 9 illustrates an enlarged planar view of an alternate embodiment of a snap-fit connection between interior stent component 604 and an exterior stent component 902. As in the embodiment described above with respect to FIG. 8, the male component (male tab 646) extends from an outermost crown 638 of the interior stent component's most distal stent strut 634. However, in this embodiment, the female component is not a recess within the exterior stent component but rather is an attached female receptacle 950 having a recess geometry that corresponds to receiving male tab 646. Female receptacle 950 extends from an innermost crown 924 of stent strut 920. Female receptacle 950 is illustrated as an "open-ended" receptacle. In another embodiment (not shown), the female component is a closed receptacle in the form of a complete ring. The closed, complete ring may be circular, oval, or elliptical.

Figure 10:
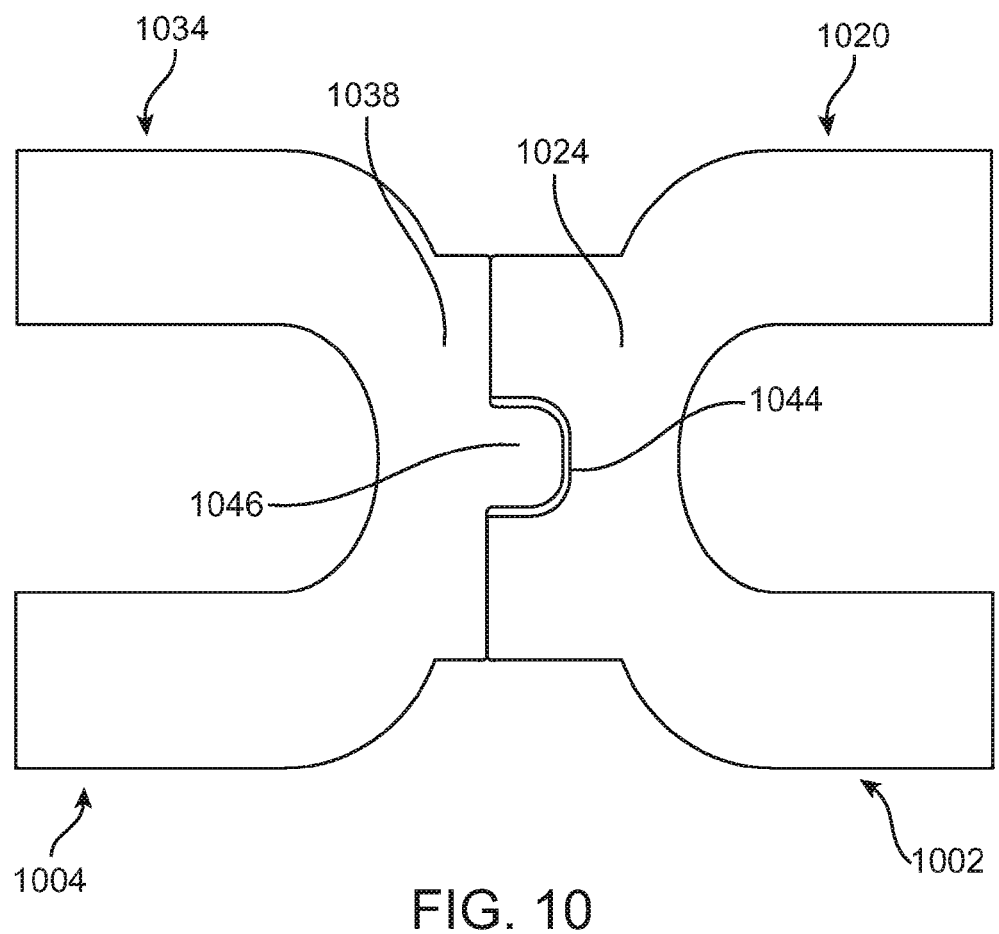
FIG. 10 is an enlarged planar view of an interference connection between an exterior stent component and an interior stent component according to another embodiment of the present invention.

FIG. 10 illustrates an enlarged planar view of an alternate interference connection between an interior stent component 1004 and an exterior stent component 1002. In this embodiment, the interference connection includes a male component (male tab 1046) extending from an outermost crown 1038 of the interior stent component's most distal stent strut 1034 and a female component (female receptacle 1044) extending within an innermost crown 1024 of stent strut 1020. The male and female components do not "snap" into place as in a snap-fit connection, but rather male tab 1046 slides or is received within female receptacle 1044 to be welded or otherwise permanently affixed thereto. The interference connection assures proper alignment of the exterior and interior stent components and minimizes or mitigates the stresses compared to other weld configuration.

Figure 11:
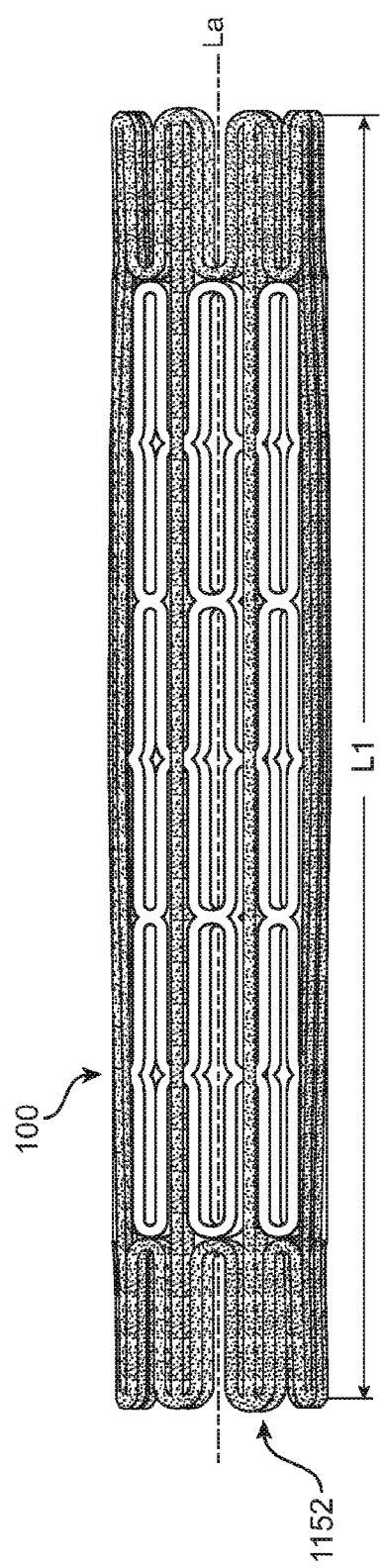
FIG. 11 shows a side view of the stent system in a contracted or compressed configuration.
Figure 12:
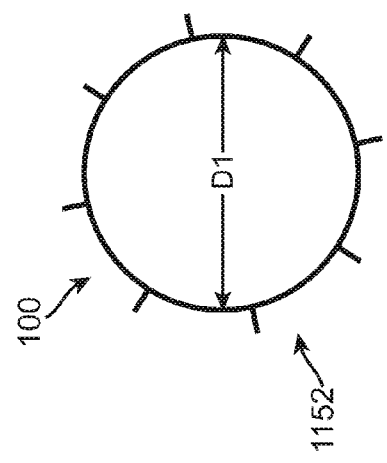
FIG. 12 illustrates an end view of the stent system in a contracted or compressed configuration.
Figure 13:
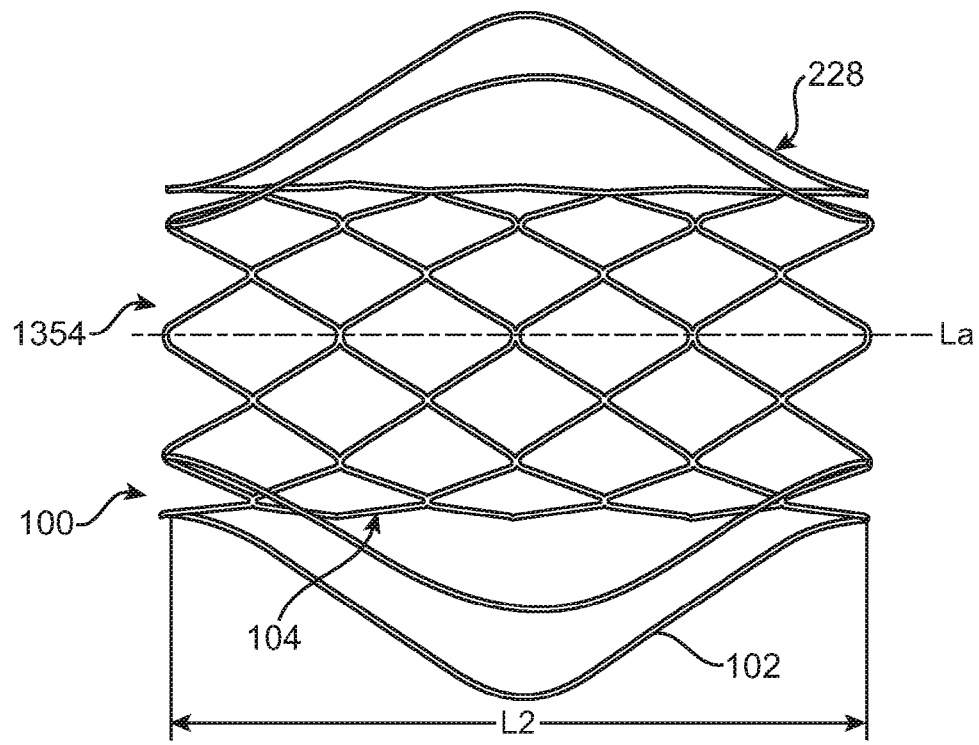
FIG. 13 shows a side view of the stent system in a deployed or expanded configuration.
Figure 14:
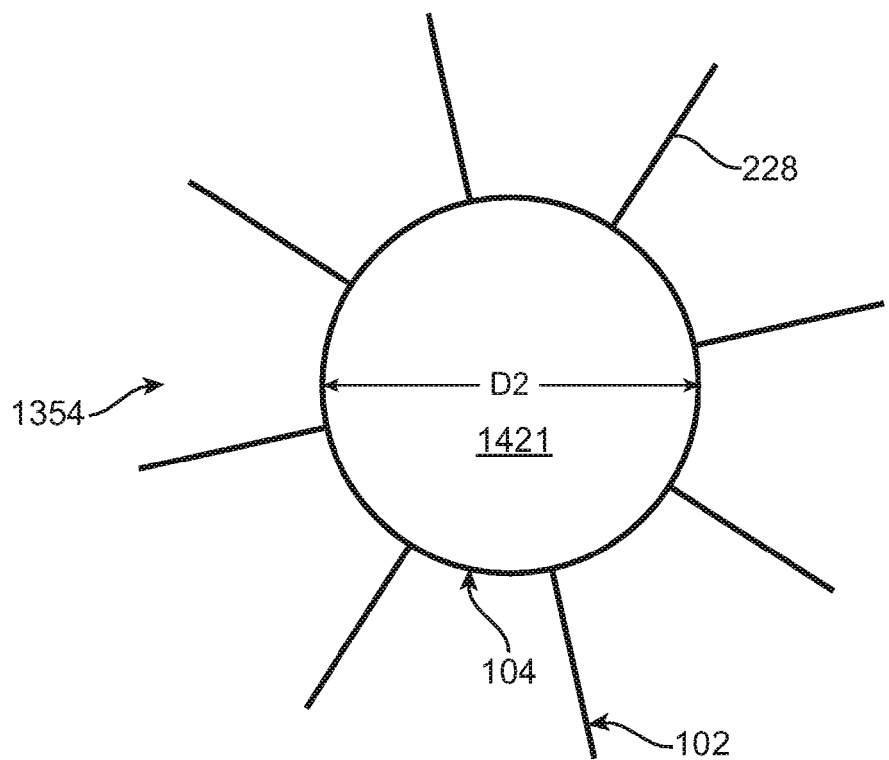
FIG. 14 illustrates an end view of the stent system in a deployed or expanded configuration.

Double walled stent system 100 has a contracted or compressed configuration 1152 sufficient for delivery to the treatment site (see FIGS. 11 and 12), and an expanded or deployed configuration 1354 (see FIGS. 13 and 14). FIG. 11 shows a side view of stent system 100 in contracted or compressed configuration 1152, while FIG. 12 illustrates an end view of stent system 100 in contracted or compressed configuration 1152. Exterior stent component 102 is crimped over interior stent component 104 in order to compress stent system 100 to a diameter D1 sufficient for delivery within a body lumen. While in contracted or compressed configuration 1152, stent system 100 has a length L1.

Referring now to FIGS. 13-14, FIG. 13 shows a side view of stent system 100 in an expanded or deployed configuration 1354, while FIG. 14 illustrates an end view of stent system 100 in expanded or deployed configuration 1354. Longitudinally-extending straight bands 228 of exterior stent component 102 are deployed or radially expanded via foreshortening dynamics of the interior stent component 104. More specifically, interior stent component 104 is designed to have a specific amount of foreshortening which reduces the length of the interior stent component upon radial expansion. As interior stent component 104 increases in diameter and decreases in length, the longitudinally-extending connectors of exterior stent component 102 bulge outwards towards the vessel wall. While in expanded or deployed configuration 1354, stent system 100 has a length L2 which is less than length L1. Stated another way, as stent system 100 radially expands, the length of stent system 100 decreases. Since the proximal and distal ends of straight bands 228 move closer together upon the foreshortening of the interior stent component 104, deployed straight bands 228 of exterior stent component 102 bow radially outward to come in contact with the vessel wall and aid in fixing stent system 100 to the treatment site. Interior stent component 104 radially expands to a diameter D2 that is greater than diameter D1 and forms a central flow lumen 1421 there through. The central flow lumen 3421 has a consistent predetermined expanded diameter to accommodate blood flow there through. For example, the consistent predetermined expanded diameter may be approximately the same as the normal diameter of the body vessel in which the stent system is to be implanted. In one embodiment, when in expanded or deployed configuration 1354, the diameter of the central flow lumen 1421 is approximately 18 mm. However, an outer surface of interior stent component 104 makes little to no contact with the vessel wall but rather remains centered inside exterior component 102 as shown in FIGS. 13-14. Interior stent component 104 is configured to be radially centered inside a body lumen, or is located mid-lumen.

Interior stent component 104 can be expanded in several ways. In one embodiment, deployment of a self-expanding stent may be facilitated by utilizing shape memory characteristics of a material such as nickel-titanium (nitinol). Shape memory metals are a group of metallic compositions that have the ability to return to a defined shape or size when subjected to certain thermal or stress conditions. Shape memory metals are generally capable of being deformed at a relatively low temperature and, upon exposure to a relatively higher temperature, return to the defined shape or size they held prior to the deformation. This enables the stent to be inserted into the body in a deformed, smaller state so that it assumes its "remembered" larger shape once it is exposed to a higher temperature, i.e., body temperature or heated fluid, in vivo. Thus, the self-expanding stent can have two states of size or shape, a contracted or compressed configuration sufficient for delivery to the treatment site and a deployed or expanded configuration for contacting the vessel wall. The interior stent component, may be formed from a heat-expandable material such as nickel-titanium (nitinol). Once placed at the treatment or deployment site, the stent system is subjected to a heat source, which causes the expansion of the interior stent component of the stent system through a chemical reaction or thermal expansion, depending upon the material from which the stent component is made. The tubular body of interior stent component is allowed to open to its heat-shaped form and foreshortening dimension, thus expanding the longitudinally-extending connectors of the exterior stent component to bow outwards and contact the vessel wall to provide the required opposition forces in the vessel.

In another embodiment, the interior stent component may be constructed out of a self-expanding spring-type or superelastic material such as nickel-titanium (nitinol) and may be collapsed or crimped from an expanded shape into the contracted or compressed configuration on a delivery catheter for delivery within the vessel. When a sleeve or sheath holding the stent system in the collapsed shape is removed, the interior stent component assumes its expanded or deployed state at the treatment site within the vessel. Expansion and foreshortening of the interior stent component causes the longitudinally-extending connectors of the exterior stent component to bow outwards and come into contact with the vessel wall.

Figure 15:
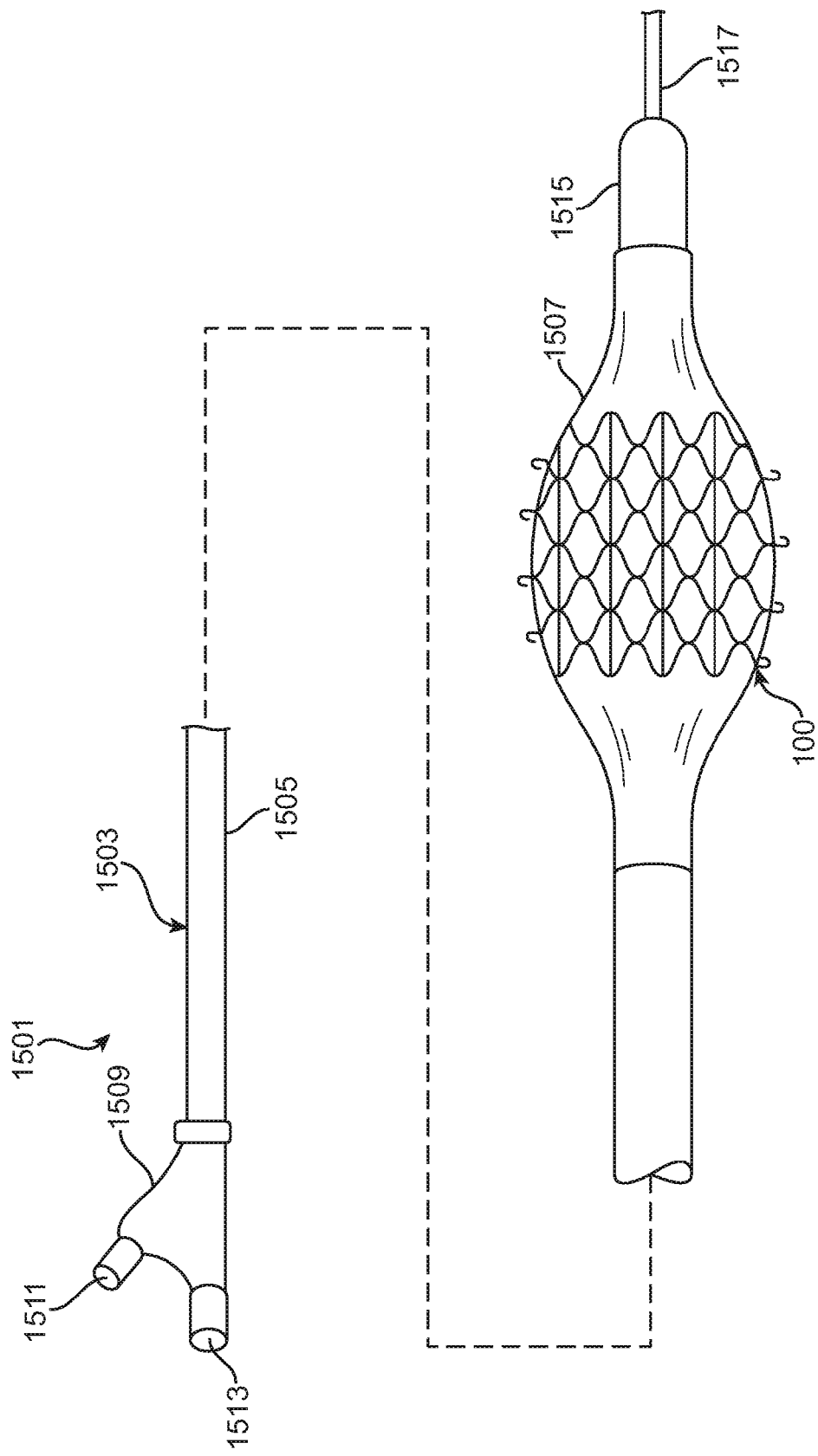
FIG. 15 illustrates a side elevational view of a delivery system for a balloon expandable stent system according to an embodiment of the present invention.

In another embodiment, the interior stent component may be balloon-expandable, such that it is crimped onto a balloon dilation catheter for delivery to a treatment site and expanded by the radial force of the balloon. More specifically, the stent system may be collapsed to a contracted or compressed configuration on top of a balloon, such as the type of balloon used in an angioplasty procedure. As the balloon expands, it physically forces the interior stent component to radially expand. Expansion and foreshortening of the interior stent component causes the longitudinally-extending connectors of the exterior stent component to bow outwards and come into contact with the vessel wall. The balloon is then collapsed leaving the stent system in the expanded or deployed configuration. For example, FIG. 15 is an illustration of a stent delivery system 1501 in accordance with an embodiment of the present invention. Stent delivery system 1501 includes an over-the-wire catheter 1503 having a proximal shaft 1505, a guidewire shaft 1515, and a balloon 1507. Proximal shaft 1505 has a proximal end attached to a hub 1509 and a distal end attached to a proximal end of balloon 1507. Guidewire shaft 1515 extends between hub 1509 and a distal tip of catheter 1503 through proximal shaft 1505 and balloon 1507. Hub 1509 includes an inflation port 1511 for coupling to a source of inflation fluid. Inflation port 1511 fluidly communicates with balloon 1507 via an inflation lumen (not shown) that extends through proximal shaft 1505. In addition, hub 1509 includes a guidewire port 1513 that communicates with a guidewire lumen (not shown) defined by guidewire shaft 1515 for receiving a guidewire 1517 there through. As described herein, guidewire shaft 1515 extends the entire length of catheter 1503 in an over-the-wire configuration. However, as would be understood by one of ordinary skill in the art, guidewire shaft 1515 may alternately extend only within the distal portion of catheter 1503 in a rapid-exchange configuration. A double walled stent system stent 100 formed in accordance with an embodiment of the present invention is positioned over balloon 1507. However, one or ordinary skill in the art can appreciate that the stent system of the present invention can be adapted for any type of delivery and expansion method. In addition, it will be understood by one of ordinary skill in the art that one stent component may be self-expandable while the other stent component is balloon-expandable.

In all embodiments, both the exterior stent component and the interior stent component of the double walled stent system are preferably constructed of implantable materials having good mechanical strength. For example, both components may be made of stainless steel, cobalt based alloys (605L, MP35N), titanium, tantalum, platinum alloys, niobium alloys, superelastic nickel-titanium alloy (nitinol), other biocompatible metals or other materials such as polymers. One widely used material for stents is stainless steel, particularly 316L stainless steel, which is particularly corrosion resistant. Although not required, one or more stent components may be selectively plated with platinum or other biocompatible material to provide improved visibility during fluoroscopy. In addition, the exterior stent component and/or the interior stent component may be selectively covered by a polyester or Dacron fabric.

Figure 16:
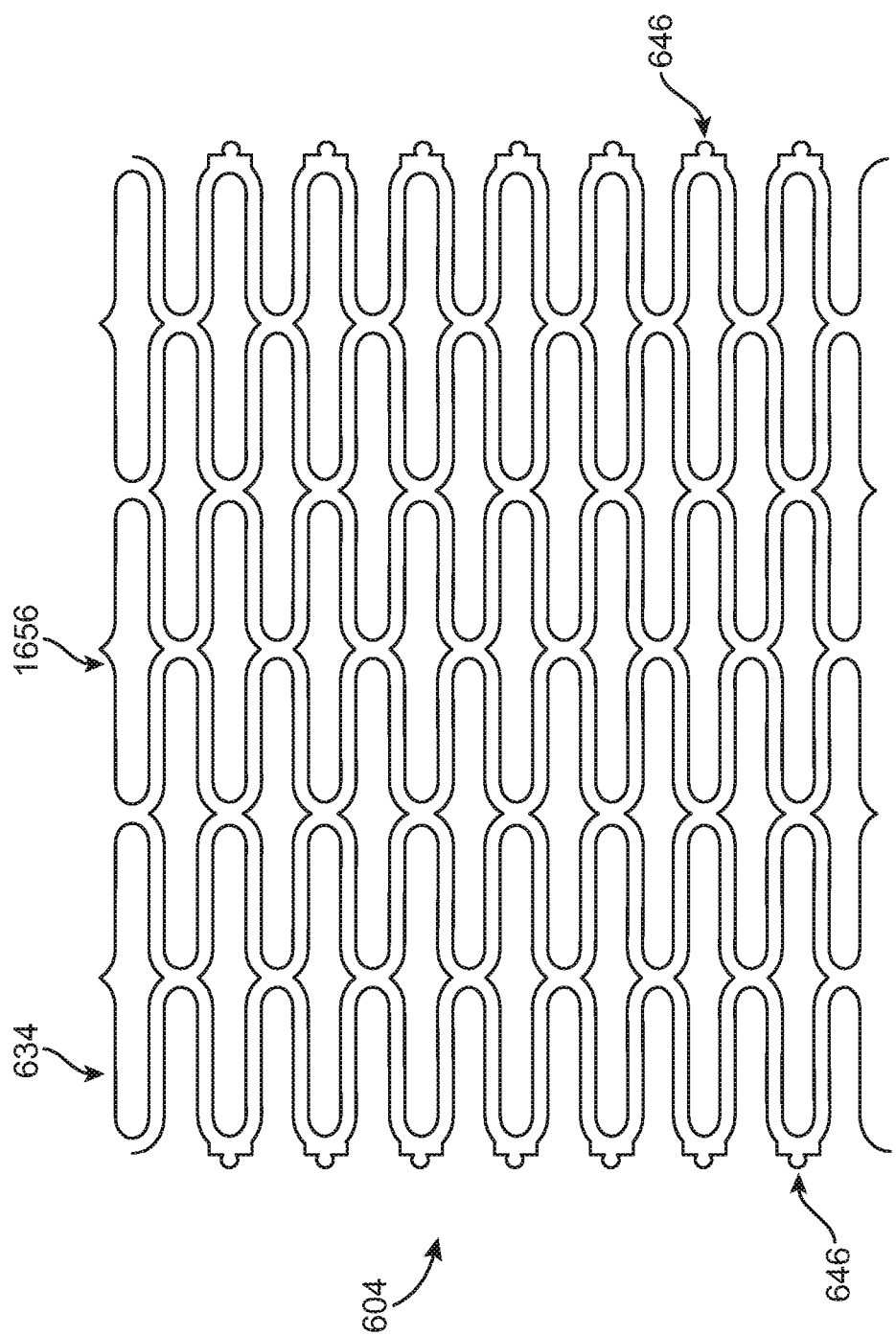
FIG. 16 is a laser-cut subcomponent for forming the interior stent component shown in FIG. 6.

Any of several conventional laser cutting methods may be used to fabricate the exterior stent component and the interior stent component into a desired shape or pattern out of a solid stock material or tubing. For example, FIG. 16 illustrates a laser cut subcomponent 1656 of interior stent component 604 of FIG. 6. Interior stent component 604 may be laser cut from MP35N tubing, or any other appropriate tubing, having an outer diameter of approximately 0.25 inches and a wall thickness of approximately 0.012 inches. Laser cut subcomponent 1656 is shown in a schematic, as if the generally circular interior stent component 604 has been cut and laid out flat. The generally cylindrical stent struts 634 are shown in a flattened state, but one skilled in the art can appreciate that the stent struts 634 depicted therein are intended to be used in a cylindrical body. When laser cut from a sheet or tube of material, stent struts 634 of interior stent component 604 may be formed connected together such that the component body is a unitary structure. As shown, male tabs 646 are also formed connected to the proximal and distal ends of interior stent component 604 such that the component is a unitary structure.

Figure 17:
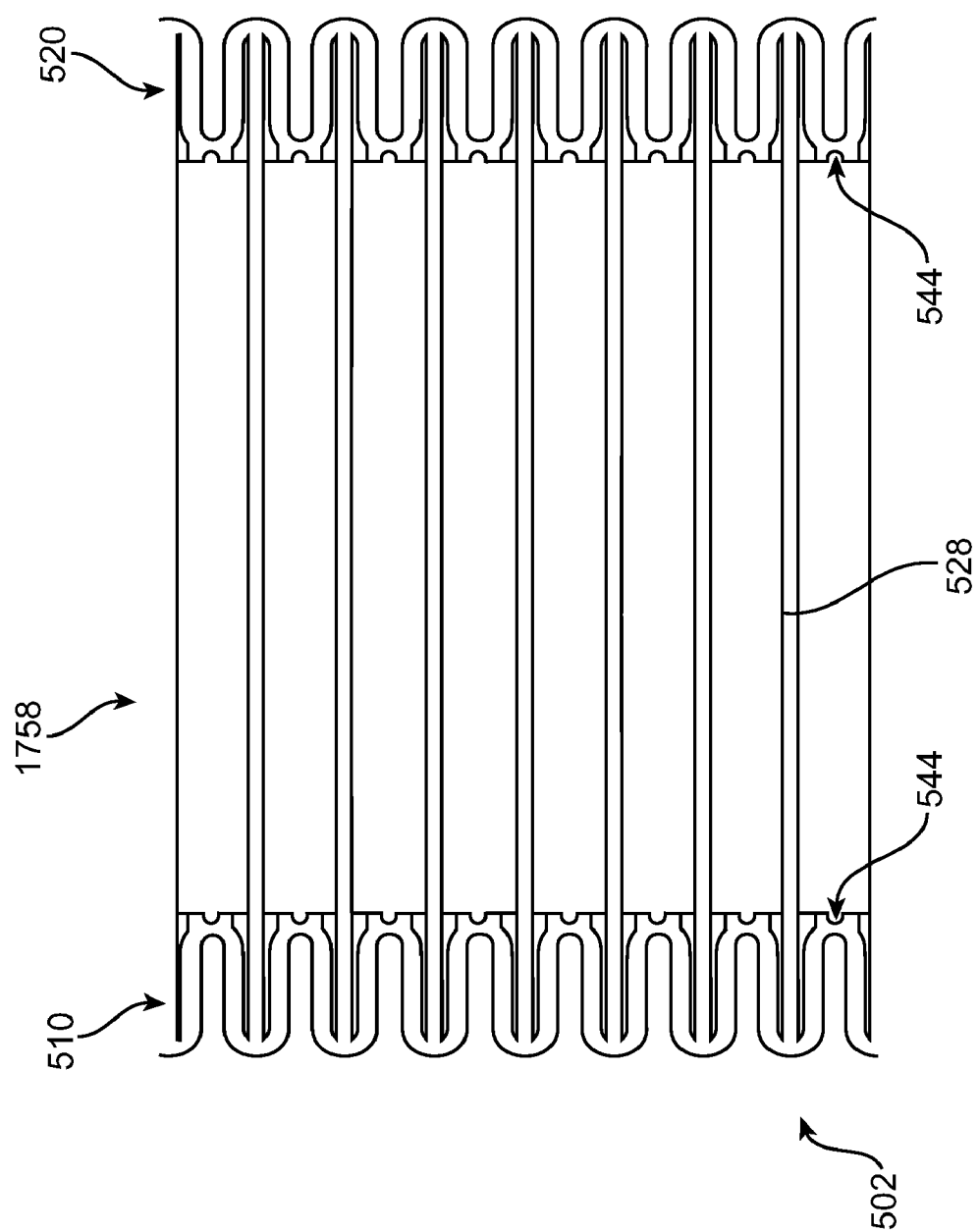
FIG. 17 is a laser-cut subcomponent for forming the exterior stent component shown in FIG. 5.

FIG. 17 illustrates a laser cut subcomponent 1758 of exterior stent component 502 of FIG. 5. Exterior stent component 502 may be laser cut from MP35N tubing, or any other appropriate tubing, having an outer diameter of approximately 0.25 inches and a wall thickness of approximately 0.012 inches. Laser cut subcomponent 1758 is shown in a schematic, as if the generally circular exterior stent component 502 has been cut and laid out flat. The generally cylindrical stent struts 510, 520 are shown in a flattened state, but one skilled in the art can appreciate that the stent struts 510, 520 depicted therein are intended to be used in a cylindrical body. When laser cut from a sheet or tube of material, stent struts 510, 520 as well as longitudinally-extending straight bands 528 of exterior stent component 502 may be formed connected together such that the component body is a unitary structure. As shown, female receptacles 544 are also formed at the proximal and distal portions of exterior stent component 502 such that the component is a unitary structure.

In addition, rather than being laser cut from any appropriate tubing material, the exterior stent component and interior stent component of the double walled stent system may be manufactured in any other method that would be apparent to one skilled in the art. For example, the stent struts may be formed by winding a wire or ribbon around a mandrel to form the pattern described above and then welding or otherwise mechanically connecting two ends thereof. The stent struts are subsequently connected together to form the interior stent component, or are connected to longitudinally-extending connectors to form the exterior stent component. Alternatively, the stents struts may be manufactured by machining tubing or solid stock material into toroid bands, and then bending the bands on a mandrel to form the desired pattern. The stent struts formed in this manner are also subsequently connected together to form the interior stent component, or are connected to longitudinally-extending connectors to form the exterior stent component. The cross-sectional shape of the finished stent system may be circular, ellipsoidal, rectangular, hexagonal rectangular, square, or other polygon, although at present it is believed that circular or ellipsoidal may be preferable.

Once the exterior stent component and the interior stent component are separately manufactured in one of the manners described above, the components are joined together in order to form the double walled stent system. The components may be welded, soldered, cryogenically coupled, or otherwise mechanically connected together. In a method of manufacture according to an embodiment of the present invention, the components are joined together by expanding the exterior stent component to a sufficient size that the interior stent component may be inserted therein. The exterior stent component is then crimped or compressed over the interior stent component to a contracted or compressed configuration. The adjacent crowns between the interior stent component and the exterior stent component are welded, soldered, cryogenically coupled, or otherwise mechanically connected together.

As explained above, the components may include corresponding male and female components that form a snap-fit or interference connection when assembled into the stent system. If male and female components of a snap-fit or interference connection are present, the components are joined together by expanding the exterior stent component to a sufficient size that the interior stent component may be inserted therein. The male component is aligned within the female component after the interior stent component is inserted within the exterior component. As such, the snap-fit or interference connection assures proper alignment of the exterior and interior stent components. The exterior stent component is then crimped or compressed over the interior stent component to a contracted or compressed configuration. The male component is then press fit into the female component. The male and female components of the snap-fit or interference connection are then welded, soldered, cryogenically coupled, or otherwise mechanically connected together.

A cryogenically coupled snap-fit connection avoids the metallurgical effects and technical difficulties of welding or fusing NiTi (Nitinol) to a dissimilar metal, such as, for example, CoCr alloys, stainless steels, MP35N alloys. For example, the female component may be formed from NiTi (Nitinol), and the male component may be made from a dissimilar metal such as one of those named above. The male and female components of the cryogenically coupled connection start by being fabricated at room temperature (austenite phase) to the final "deployed" coupled dimensions. To produce the desired coupling effect, the temperature of the female component is lowered well below its Transition Temperature (TT) and driven into the martensitic phase. In practice, this can be accomplished by soaking the component in a liquid nitrogen bath. Whilst in this state, the hole or recess of the female component is radially expanded or enlarged by forcing an oversized tapered mandrel longitudinally there through. When continually cooled below the transition temperature, the female component remains stably expanded. Coupling the female component with the male component is then accomplished by inserting the end of the male component into the expanded female component and allowing the female component to warm to its near original, or memory, diameter. The radial contraction of the female component, and the associated chronic force, provides a continuously clamping joint above the transition temperature, designed to be well below body temperature or 37° C. When the female component has an "open-ended" receptacle such as in the embodiments depicted in FIGS. 8-10, a wedge effect will prevent the male component from passing through from the outer diameter of the female component to the inner diameter of the female component in the radial direction. In another embodiment, the female component is a closed receptacle in the form of a complete ring. The ring may be circular, oval, or elliptical. The male component passes through the closed receptacle of the female component and experiences interference in radial, axial, or combined directions.

Figure 18A:
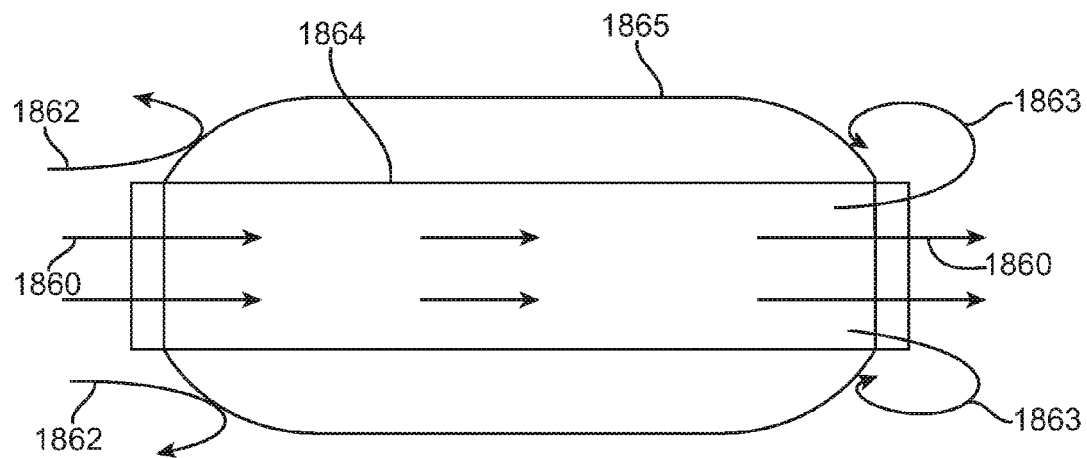
FIG. 18A is a diagrammatical illustration of flow through a double walled stent system according to an embodiment of the present invention.

As described above, in some embodiments of the present invention, the exterior stent component includes proximal and distal stent struts connected to each other via longitudinally-extending connectors. In another embodiment, flared stent struts may be attached to the proximal and distal portions of the exterior stent component in order to prevent stent migration and valve leakage. More particularly, with reference to FIGS. 18A-18B, flow through a "straight" double walled stent system is compared to flow through a "flared" double walled stent system. The interior stent component is represented by a tubular segment 1864, while the exterior stent component is represented by an elongated oval shape segment 1865. FIG. 18A illustrates flow represented by arrows 1860 through a tubular segment 1864 having straight ends. Flow 1860 is primarily directed straight through the system. However, due to the relatively smaller inlet of tubular segment 1864, some of the flow represented by arrows 1862 "misses" the inlet and swirls/rolls off the sides of segment 1865 at the proximal end of the system. Similarly, due to the relatively smaller outlet of tubular segment 1864, some of the flow represented by arrows 1863 reverses and swirls/rolls off the sides of segment 1865 at the distal end of the system. Flow 1862 may cause unwanted rotational migration of the system, as well as a phenomenon known as "watermelon seeding" which causes the system to migrate distally an unpredictable distance.

Figure 18B:
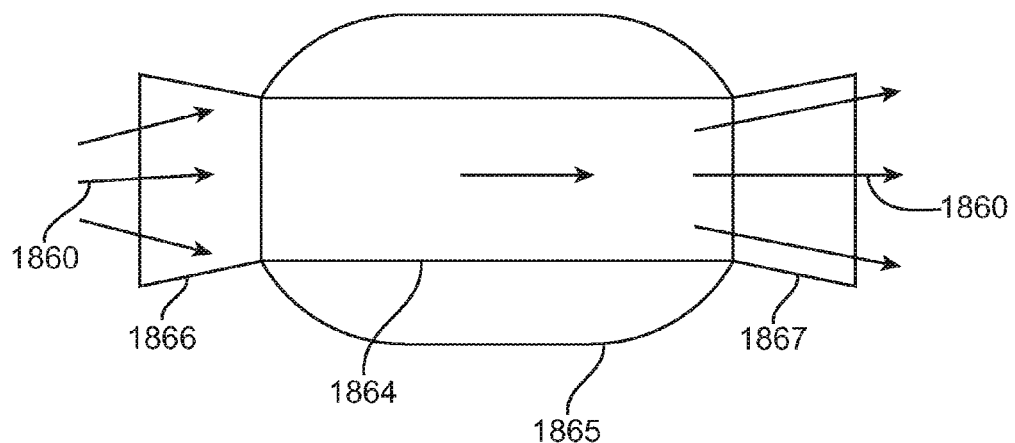
FIG. 18B is a diagrammatical illustration of flow through a double walled stent system according to another embodiment of the present invention.

In comparison, flared end segments may help prevent such unwanted migration, and may be formed at an appropriate length and flare angle to prevent hemostasis and subsequent thrombogenic effects. FIG. 18B illustrates flow represented by arrows 1860 through a tubular segment 1864 having flared ends 1866. Due to the relatively larger inlet of flared inlet end 1866, flow 1860 is directed straight through the system at the proximal end of the system. Similarly, due to the relatively larger outlet of flared outlet end 1867, flow 1860 is directed straight out of the system at the distal end of the system.

Figure 19:
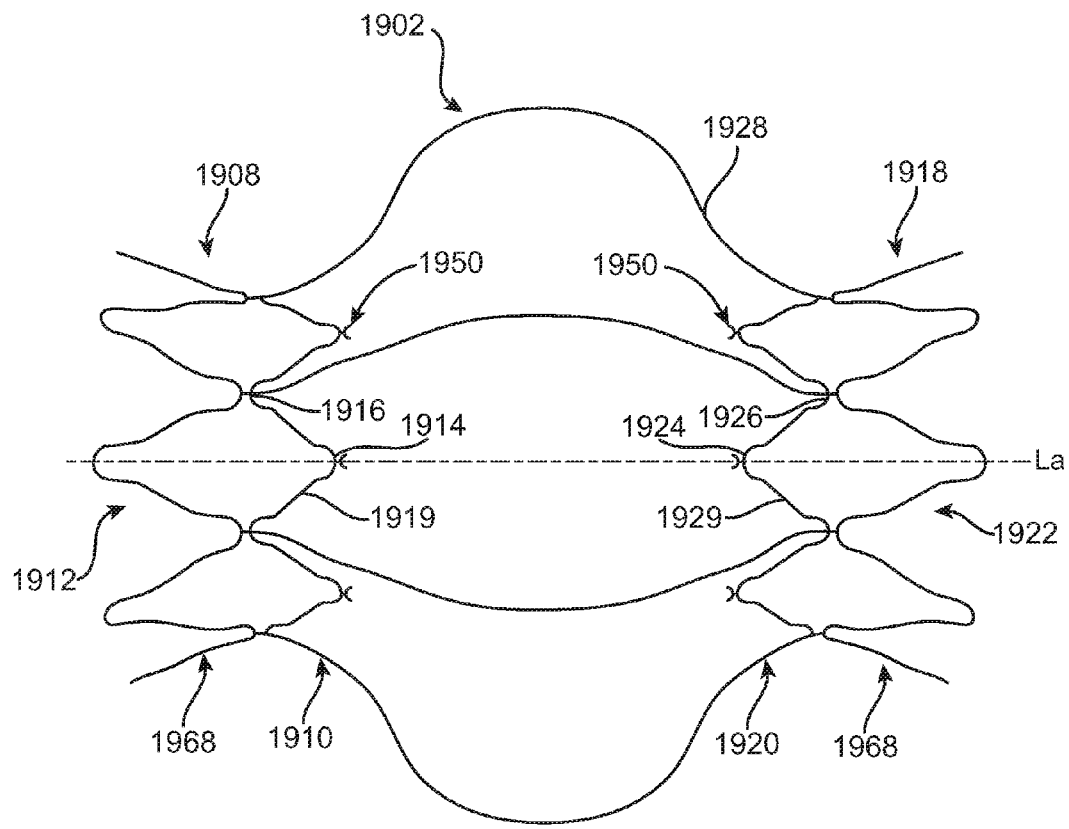
FIG. 19 shows a side view of an exterior stent component in a deployed or expanded configuration according to another embodiment of the present invention.

FIG. 19 shows a side view of an exterior stent component 1902 having flared stent struts 1968 at its proximal and distal ends. Exterior stent component 1902 has a proximal portion 1908 and a distal portion 1918. Similar to exterior stent component 102, proximal portion 1908 includes a generally cylindrical stent strut 1910 and distal portion 1918 includes a generally cylindrical stent strut 1920. Stent strut 1910 at proximal portion 1908 of exterior stent component 1902 is a wavelike or sinusoidal cylindrical band or ring having a pattern of straight segments 1919 with crowns 1914 connecting adjacent straight segments 1919, and stent strut 1920 at distal portion 1918 of exterior stent component 1902 is a wavelike or sinusoidal cylindrical band or ring having a pattern of straight segments 1929 and crowns 1924 connecting adjacent straight segments 1929. Proximal and distal stent struts 1910, 1920 are aligned on common longitudinal axis $L_a$ and are connected by a plurality of longitudinally-extending connectors such as straight bands 1928. Straight bands 1928 are generally straight strips or planks of material extending parallel to common longitudinal axis $L_a$ from a valley 1916 of crown 1914 of stent strut 1910 to an opposing valley 1926 of crown 1924 of stent strut 1920. However, unlike exterior stent component 102, the embodiment depicted in FIG. 19 includes flared stent struts 1968 at the proximal end 1912 and the distal end 1922 of exterior stent component 1902. Flared stent struts 1968 are connected to proximal and distal stent struts 1910, 1920 and radially flare such that proximal and distal ends 1912, 1922 are approximately at a twenty degrees angle from longitudinal axis $L_a$. Thus, the outer diameter of the flared stent struts 1968 at proximal and distal ends 1912, 1922 is greater than the outer diameter of proximal and distal stent struts 1910, 1920. In addition, the straight segments of flared stent struts 1968 may be longer than the straight segments 1919, 1929 of proximal and distal stent struts 1910, 1920, respectively, and the crowns of flared stent struts 1968 may be larger than the crowns 1914, 1924 of proximal and distal stent struts 1910, 1920, respectively. Flared stent struts 1968 prevent unwanted rotational stent migration and watermelon seeding, as well as may prevent hemostasis and subsequent thrombogenic effects. In addition, FIG. 19 shows exterior stent component 1902 configured to be connected to an interior stent component by the inclusion of attached female receptacles 1950 located at both the innermost crowns 1914 of proximal stent strut 1910 and the innermost crowns 1924 of distal stent strut 1920.

Figure 20:
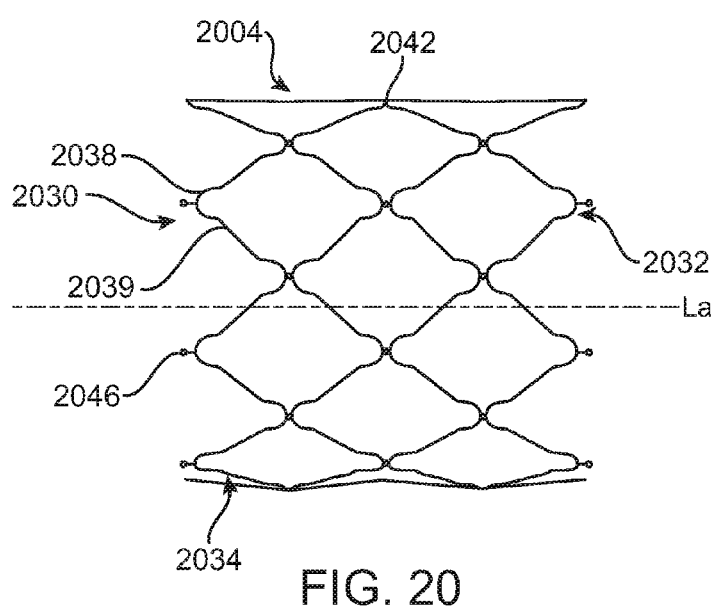
FIG. 20 shows a side view of an interior stent component in a deployed or expanded configuration according to another embodiment of the present invention.

A double walled stent system utilizing exterior stent component 1902 having the addition of flared stent struts 1968 on the ends thereof may be used in conjunction with an interior stent component having four stent struts, such that the stent system maintains a total of eight stent struts. For example, FIG. 20 illustrates an interior stent component 2004 that may be used with an exterior stent component having flared ends. Interior stent component 2004 is a cylindrically-shaped tubular body having longitudinal axis $L_a$, a proximal end 2030, and a distal end 2032. Longitudinal axis $L_a$ extends within the cylindrical body from proximal end 2030 to distal end 2032 of interior stent component 2004. A plurality of adjacent stent struts 2034 are aligned substantially parallel relative to longitudinal axis $L_a$ so as to form the cylindrically-shaped tubular body of interior stent component 2004. Each stent strut 2034 is a wavelike or sinusoidal cylindrical band or ring having a pattern of straight segments 2039 and crowns 2038 connecting adjacent straight segments 2039. FIG. 20 shows interior stent component 2004 having four stent struts 2034 connected at connections 2042. In addition, FIG. 20 shows interior stent component 2004 configured to be connected to an exterior stent component by the inclusion of male tabs 2046 located at both proximal end 2030 and distal end 2032 of interior stent component 2004.

In further embodiments of the present invention, the longitudinally-extending connectors that connect the proximal portion of the exterior stent component to the distal portion of the exterior stent component have several possible embodiments. As previously described, the longitudinally-extending connectors of the exterior stent component come in contact with the vessel wall when deployed in order to aid in fixing the stent system to the treatment site. Since the interior stent component remains radially centered within the body lumen, the double walled stent system is particularly suited for treating anomalies of the right ventricular outflow tract because the longitudinally-extending connectors of the exterior stent component bow radially outward in order to ensure that the system is fixed against the vessel wall despite potential patient growth and/or anomalies of a vessel. As previously described above in relation to embodiments of the exterior stent component, the longitudinally-extending connectors may be generally straight bands of material extending from the proximal end to the distal end of the exterior stent component. In further embodiments of the present invention described in more detail below, the longitudinally-extending connectors of the exterior stent component are a plurality of wavelike or sinusoidal bands or spars that are longitudinally and radially collapsible. The sinusoidal bands or spars of adjacent longitudinally-extending connectors may be nested within each other. The longitudinally-extending connectors may extend generally parallel to a longitudinal axis of the exterior stent component, may extend at a slant or angle with respect to a longitudinal axis of the exterior stent component, or may extend in a helical fashion around the longitudinal axis of the exterior stent component.

Figure 21:
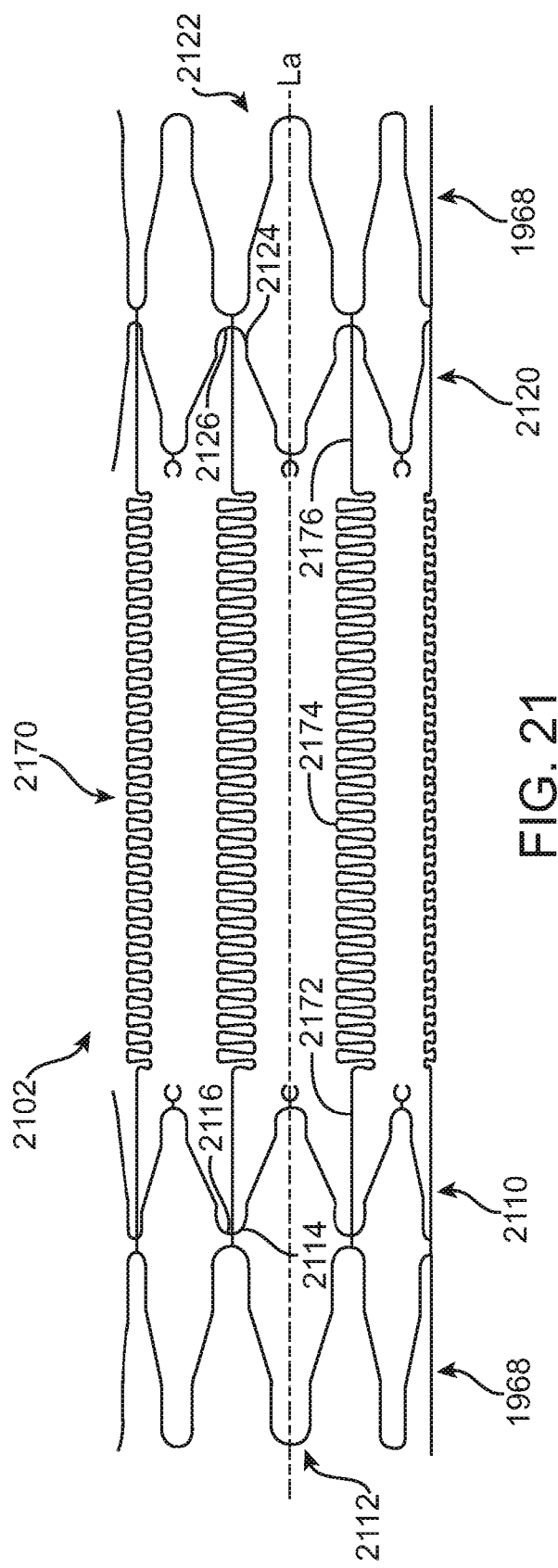
FIG. 21 shows a side view of an exterior stent component according to another embodiment of the present invention.

For example, FIG. 21 shows a side view of an exterior stent component 2102 including longitudinally-extending connectors according to another embodiment of the present invention. In this embodiment, the longitudinally-extending connectors are connector bands 2170. Connector bands 2170 include a straight proximal section 2172, a wavelike or sinusoidal intermediate section 2174, and a straight distal section 2176. Wavelike or sinusoidal intermediate section 2174 provide both additional surface area and pockets to allow for tissue in growth that will further aid in fixing the stent system to the vessel wall and avoid stent migration after deployment. Connector bands 2170 extend generally parallel to common longitudinal axis $L_a$ from a valley 2116 of crown 2114 of stent strut 2110 to an opposing valley 2126 of crown 2124 of stent strut 2120. Straight proximal and distal sections 2172, 2176 have a length approximately equal to the length of a straight segment of stent struts 2110, 2120, while sinusoidal intermediate section 2174 has a length approximately equal to the length of an interior stent component such that sinusoidal intermediate section 2174 generally extends over the entire length of the interior stent component once assembled. Although the embodiment depicted in FIG. 21 includes flared stent segments 1968 at proximal end 2112 and distal end 2122 of exterior stent component 2102, it will be understood that connector bands 2170 may be used as the longitudinally-extending connectors for any embodiment of the exterior stent component described herein.

Figure 22:
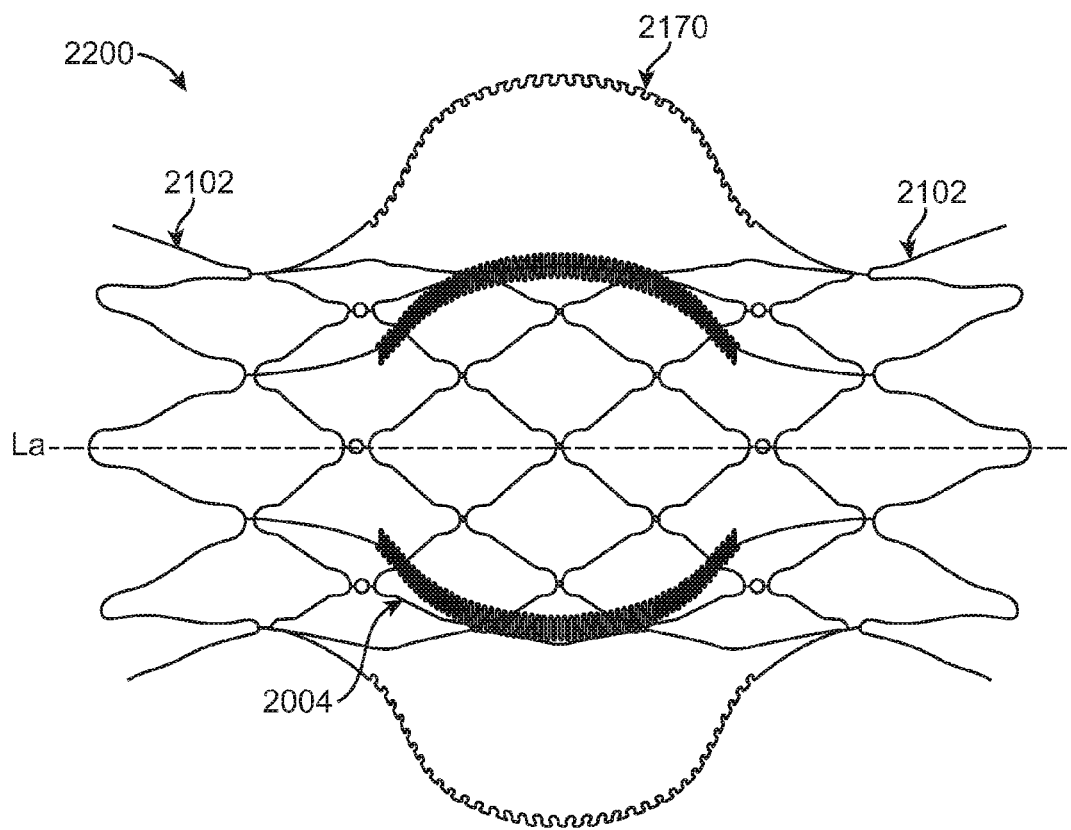
FIG. 22 shows a side view of a double walled stent system including the interior stent component of FIG. 20 and the exterior stent component of FIG. 21 in a deployed or expanded configuration.
Figure 23:
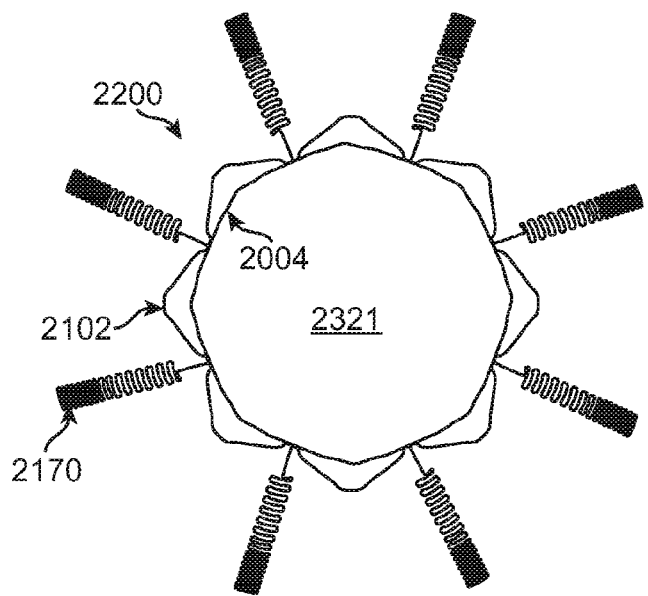
FIG. 23 shows an end view of the double walled stent system of FIG. 22.

FIG. 22 shows a side view of a double walled stent system 2200 in an expanded or deployed configuration, while FIG. 23 illustrates an end view of stent system 2200 in the expanded or deployed configuration. Stent system 2200 includes exterior stent component 2102 (of FIG. 21) and interior stent component 2004 (of FIG. 20) connected thereto. Exterior stent component 2102 includes wavelike connector bands 2170 deployed in order to aid in fixing the stent system to the treatment site. Interior stent component 2004 defining a central flow lumen 2321 is shown in the expanded or deployed configuration radially centered within exterior stent component 2102. Although the embodiment depicted in FIGS. 22-23 includes an interior stent component having four stent struts, it will be understood that the interior stent component may include any number of stent struts depending on a desired overall length of the system and/or desired mechanical properties.

Figure 24:
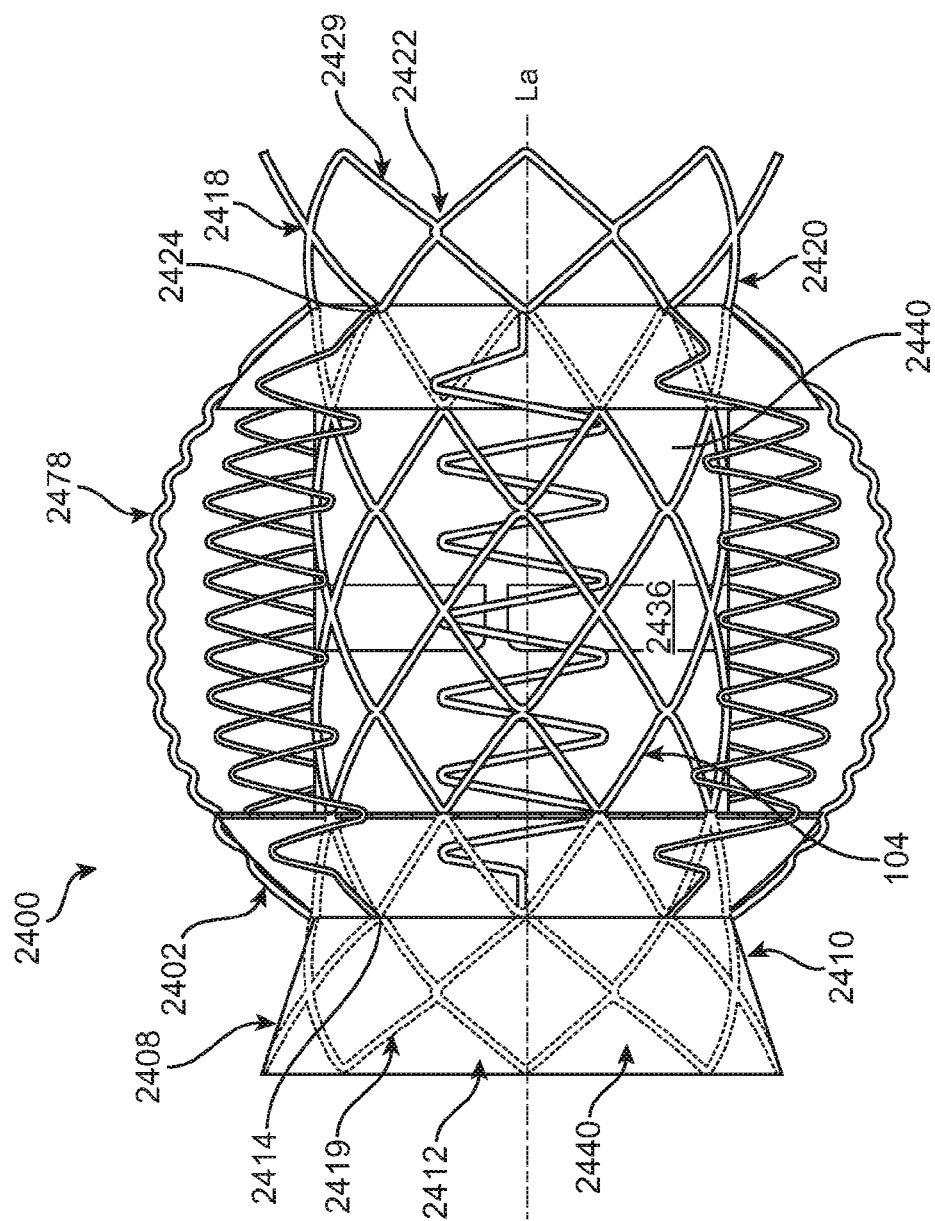
FIG. 24 shows a side view of a double walled stent system in a deployed or expanded configuration according to another embodiment of the present invention.

In FIGS. 22-23, as well as other embodiments previously described, the longitudinally-extending connectors are valley-to-valley connectors, meaning that they extend from a valley of the proximal stent strut to a valley of distal stent strut. However, the longitudinally-extending connectors may be "crown-to-crown" connectors in that they extend from a crown of the proximal stent strut to a crown of the distal stent strut. For example, FIG. 24 shows a side view of a double walled stent system 2400 in a deployed or expanded configuration according to another embodiment of the present invention. Stent system 2400 includes an exterior stent component 2402 connected to interior stent component 104. Exterior stent component 2402 has a proximal portion 2408 and a distal portion 2418. Proximal portion 2408 includes two connected generally cylindrical stent struts 2410 and distal portion 2418 includes two connected generally cylindrical stent struts 2420. Although shown with two connected stent struts at proximal and distal portions, it will be understood that the proximal and distal portions of the exterior stent component may include any number of stent struts. Stent struts 2410 at proximal portion 2408 of exterior stent component 2402 are wavelike or sinusoidal cylindrical bands or rings having a pattern of straight segments 2419 with crowns 2414 connecting adjacent straight segments 2419, and stent struts 2420 at distal portion 2418 of exterior stent component 2402 are wavelike or sinusoidal cylindrical bands or rings having a pattern of straight segments 2429 and crowns 2424 connecting adjacent straight segments 2429. Proximal and distal stent struts 2410, 2420 are aligned on common longitudinal axis $L_a$ and radially flare such that proximal and distal ends 2412, 2422 of exterior stent component 2402 are approximately at a twenty degrees angle from longitudinal axis $L_a$. Thus, the outer diameter of the flared stent struts 2410, 2420 at proximal and distal ends 2412, 2422 is greater than the outer diameter of the interior stent component 104. Flared stent struts 2410, 2420 prevent unwanted rotational stent migration and watermelon seeding, as well as may prevent hemostasis and subsequent thrombogenic effects.

Flared stent struts 2410, 2420 are connected by a plurality of longitudinally-extending connectors extending parallel to common longitudinal axis $L_a$. The longitudinally-extending connectors of exterior stent component 2402 are a plurality of wavelike or sinusoidal bands 2478 that extend from an innermost crown 2414 of proximal stent strut 2410 to an opposing innermost crown 2424 of distal stent strut 2420. Wavelike or sinusoidal intermediate bands 2478 provide both additional surface area and pockets to allow for tissue in growth that will further aid in fixing the stent system to the vessel wall and avoid stent migration after deployment. As crown-to-crown connectors, sinusoidal bands 2478 have a length approximately equal to the length of interior stent component 104 such that interior stent component 104 may be positioned between stent struts 2410, 2420. Sinusoidal bands 2478 may nest within each other when unexpanded (not shown) as explained below with respect to the embodiment of FIG. 28. In addition, stent system 2400 illustrates a valve 2436 within the interior stent component 104 to regulate flow there through. Valve 2436 may be a bovine or porcine valve treated and prepared for use in a human, or may be a mechanical valve or a synthetic leaflet valve. When a valve is utilized within the interior stent component, it is required that the interior stent component act as a blood flow conduit for directing blood flow through the center of the device and restricting blood flow from the outer walls of the stent system. In order to act as a blood flow conduit, a valve may be used in conjunction with a graft, or a bovine or porcine valve may retain the native conduit. Stent system 2400 also illustrates graft material 2440 enclosing proximal stent struts 2410 of exterior stent component 2402, as well as on the interior surface of interior stent component 104. Valve 2436 may be sealingly and permanently attached to graft material 2440 and/or interior stent component 104. Graft material 2440 may be a low-porosity woven fabric, such as polyester, Dacron fabric, or PTFE, which creates a one-way fluid passage when attached to interior stent component 104.

Figure 37:
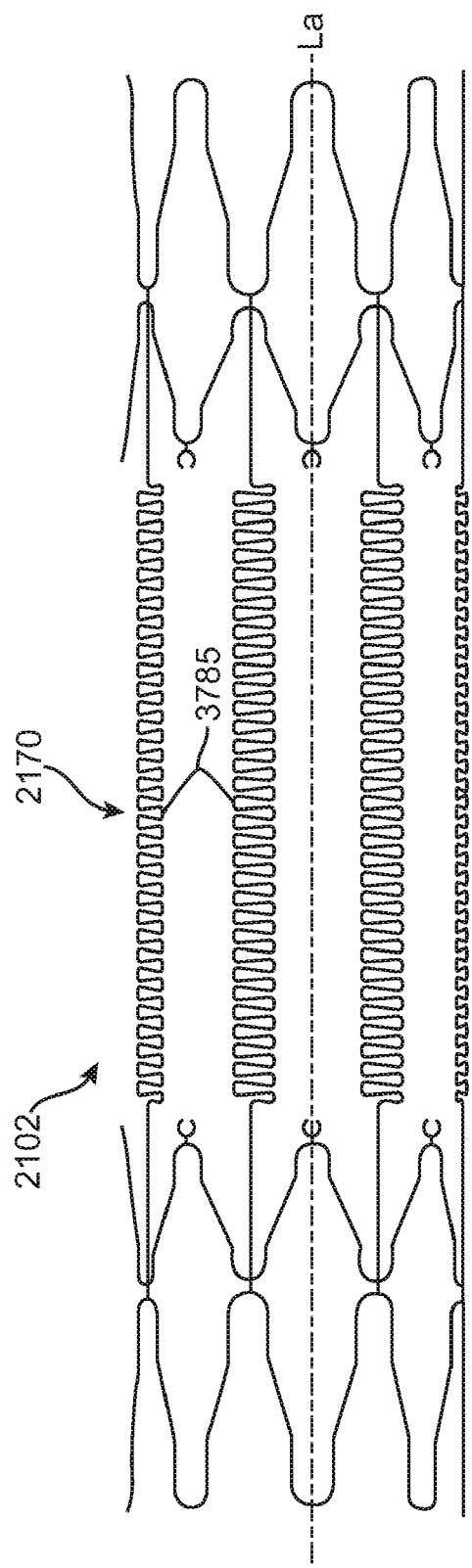
FIG. 37 is a side view of the exterior stent component of FIG. 21, wherein the stent component includes an intermediate connector or tether between adjacent longitudinally-extending connectors according to an embodiment of the present invention.
Figure 38:
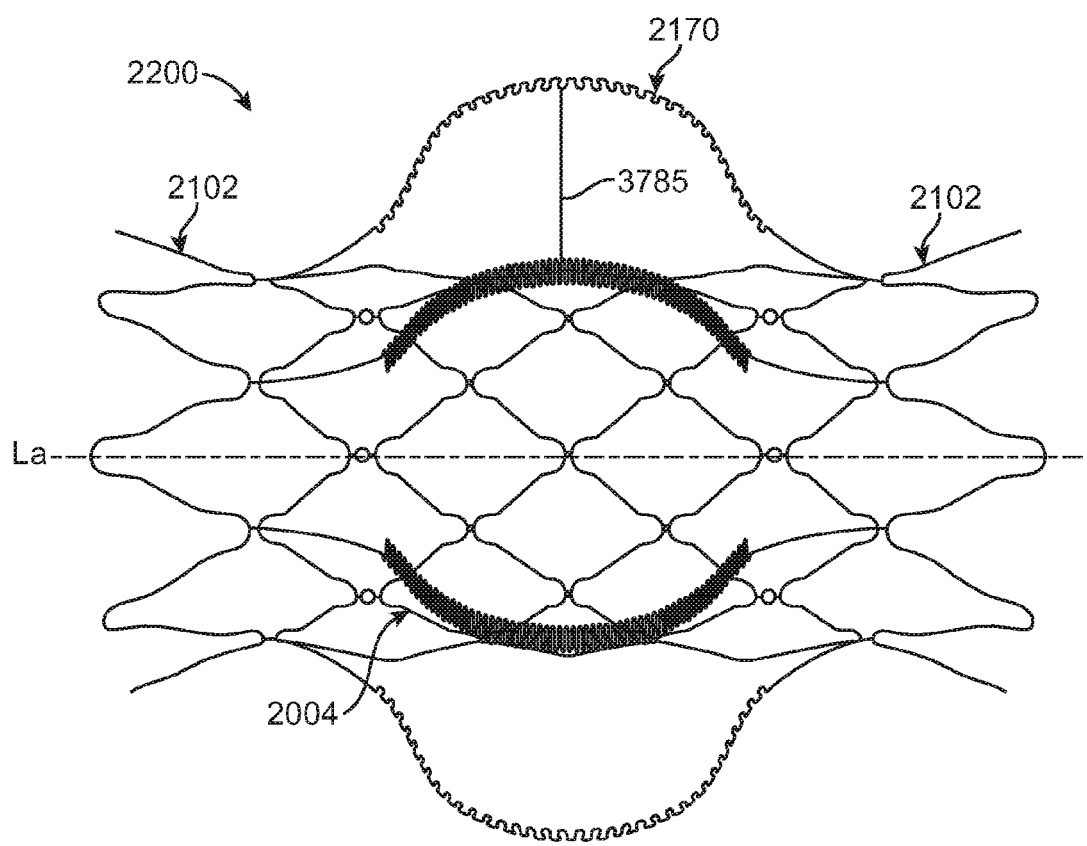
FIG. 38 shows a side view of a double walled stent system including the interior stent component of FIG. 20 and the exterior stent component of FIG. 37 in a deployed or expanded configuration.

In another embodiment of the present invention, the exterior stent component may include one or more lateral connectors for attaching adjacent longitudinally-extending connectors. The utilization of a lateral connector is intended to laterally stabilize the longitudinally-extending connectors by preventing them from folding over onto themselves due to forces exerted by the vessel wall. In addition, the lateral connector will provide additional scaffolding or support for the vessel wall and additional fixation advantages. In one embodiment of the present invention, the lateral connector may simply be a tether connecting the longitudinally-extending connectors together. For example, FIG. 37 shows exterior stent component 2102, previously described with respect to FIG. 21, having a tether 3785 serving as an intermediate connector between wavelike connector bands 2170 of exterior stent component 2102. FIG. 37 shows tether 3785 in a collapsed or unexpanded configuration such that tether 3785 has a U-shape or a V-shape. FIG. 38 illustrates double walled stent system 2200 in an expanded or deployed configuration, wherein tether 3785 is radially expanded and stretched to a straightened configuration between adjacent wavelike connector bands 2170 of exterior stent component 2102. Deployed stent system 2200 includes exterior stent component 2102 and interior stent component 2004 of FIG. 20 connected thereto. Interior stent component 2004 is shown in the expanded or deployed configuration radially centered within exterior stent component 2102. Although FIGS. 37-38 illustrate only one lateral connector to connect adjacent longitudinally-extending connectors, in various other embodiments multiple connectors may be used to connect multiple pairs of adjacent longitudinally-extending connectors.

Figure 25:
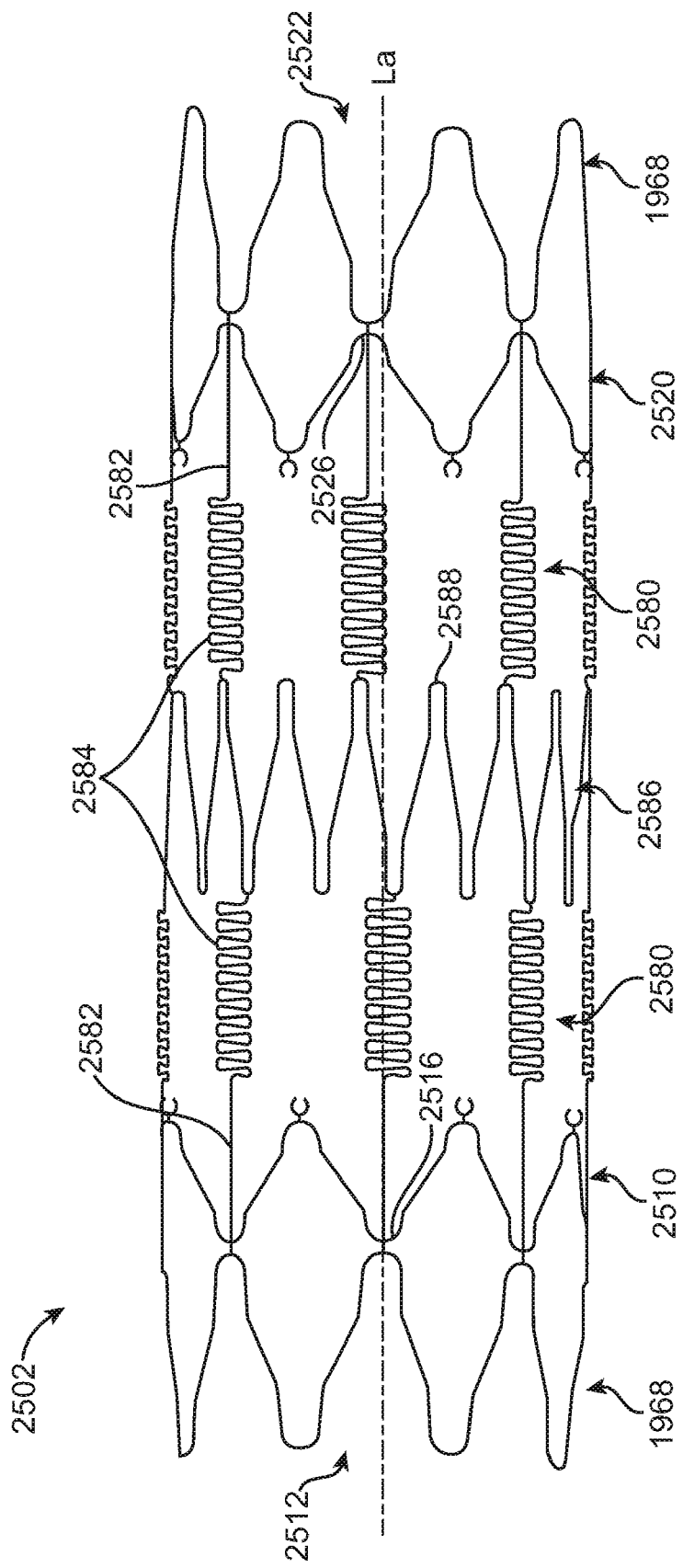
FIG. 25 shows a side view of an exterior stent component according to another embodiment of the present invention.

In another embodiment of the present invention, an intermediate stent strut is located between the proximal and distal stent struts, and longitudinally-extending connectors connect the proximal stent strut to the intermediate stent strut as well as the intermediate stent strut to the distal stent strut. For example, FIG. 25 shows a side view of an exterior stent component 2502. In this embodiment, in addition to stent struts 2510, 2520 at the proximal and distal portions, exterior stent component 2502 also includes an intermediate stent strut 2586. Intermediate stent strut 2586 is a wavelike or sinusoidal cylindrical band or ring having a pattern of straight segments and crowns 2588 connecting adjacent straight segments, the intermediate strut is aligned substantially parallel relative to longitudinal axis $L_a$ of stent struts 2510, 2520. In one embodiment, intermediate stent strut 2586 has a total of sixteen crowns or twice the number of crowns as each of proximal and distal stent struts 2510, 2520. Longitudinally-extending connectors connect proximal stent strut 2510 to intermediate stent strut 2586, and also connect intermediate stent strut 2586 to distal stent strut 2520. In the embodiment of FIG. 25, the longitudinally-extending connectors are two sets of connector bands 2580, such that one set connects the proximal stent strut 2510 to intermediate stent strut 2586 and the other set connects the distal stent strut 2520 to intermediate stent strut 2586.

Each connector band 2580 includes a straight section 2582 and a wavelike or sinusoidal section 2584. Wavelike or sinusoidal intermediate sections 2584 provide both additional surface area and pockets to allow for tissue in growth that will further aid in fixing the stent system to the vessel wall and avoid stent migration after deployment. Connector bands 2580 extend generally parallel to common longitudinal axis $L_a$ from a valley 2516/2526 of stent strut 2510/2520 to an opposing crown 2588 of intermediate stent strut 2586. Straight sections 2582 have a length approximately equal to the length of a straight segment of stent struts 2510, 2520, while sinusoidal section 2584 has a length sufficient to reach the opposing crown of intermediate stent strut 2586. Although the embodiment depicted in FIG. 25 includes flared stent segments 1968 at proximal end 2512 and distal end 2522 of exterior stent component 2502, it will be understood that connector band 2580 may be used as the longitudinally-extending connectors for any embodiment of the exterior stent component described herein.

Figure 26:
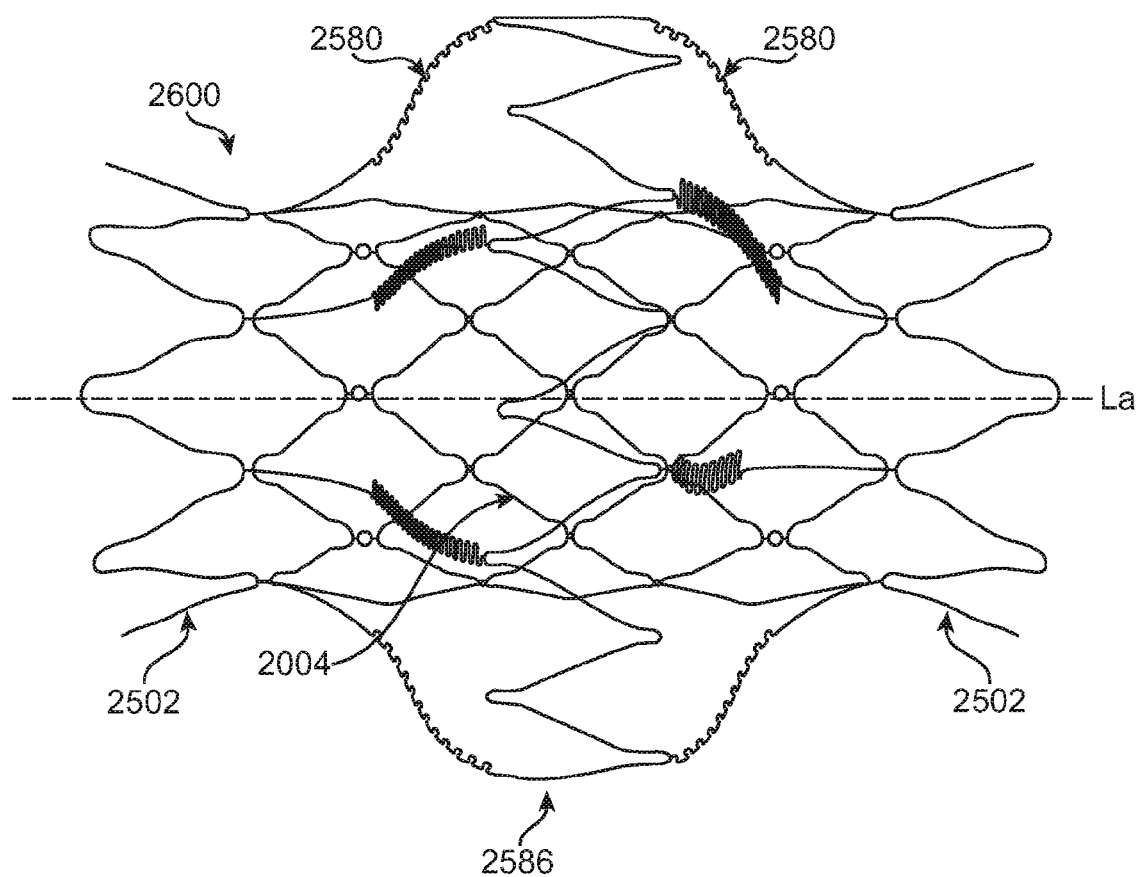
FIG. 26 shows a side view of a double walled stent system including the interior stent component of FIG. 20 and the exterior stent component of FIG. 25 in a deployed or expanded configuration.
Figure 27:
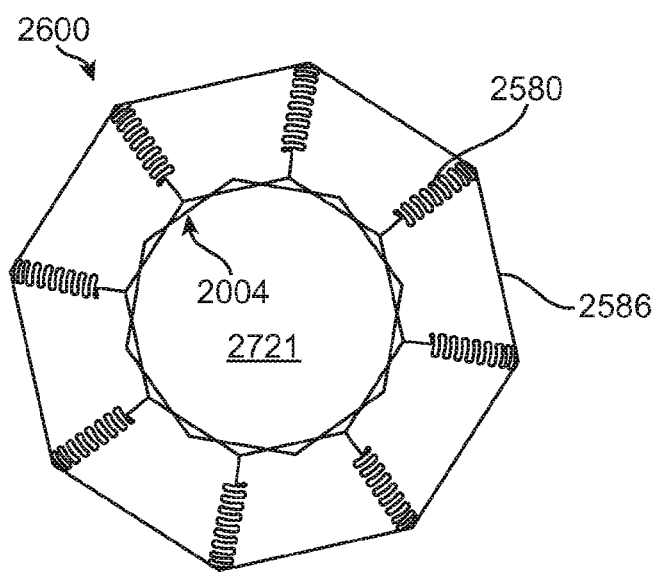
FIG. 27 shows an end view of the double walled stent system of FIG. 26.

FIG. 26 shows a side view of a double walled stent system 2600 in an expanded or deployed configuration, while FIG. 27 illustrates an end view of stent system 2600 in the expanded or deployed configuration. Stent system 2600 includes exterior stent component 2502 (of FIG. 25) and interior stent component 2004 (of FIG. 20) connected thereto. Exterior stent component 2502 includes intermediate stent strut 2586 and two sets of connector bands 2580 deployed in order to aid in fixing the stent system to the treatment site. Intermediate stent strut 2586 has an expanded outer diameter sufficient to contact the vessel wall when expanded while simultaneously allowing interior stent component 2004 to be properly positioned mid-lumen within the vessel. The addition of intermediate stent strut 2586 allows for further support against the vessel wall. Interior stent component 2004 defining a central flow lumen 2721 is shown in the expanded or deployed configuration radially centered within exterior stent component 2502. Although the embodiment depicted in FIGS. 26-27 includes an interior stent component having four stent struts, it will be understood that the interior stent component may include any number of stent struts depending on a desired overall length of the system and/or desired mechanical properties.

Figure 28:
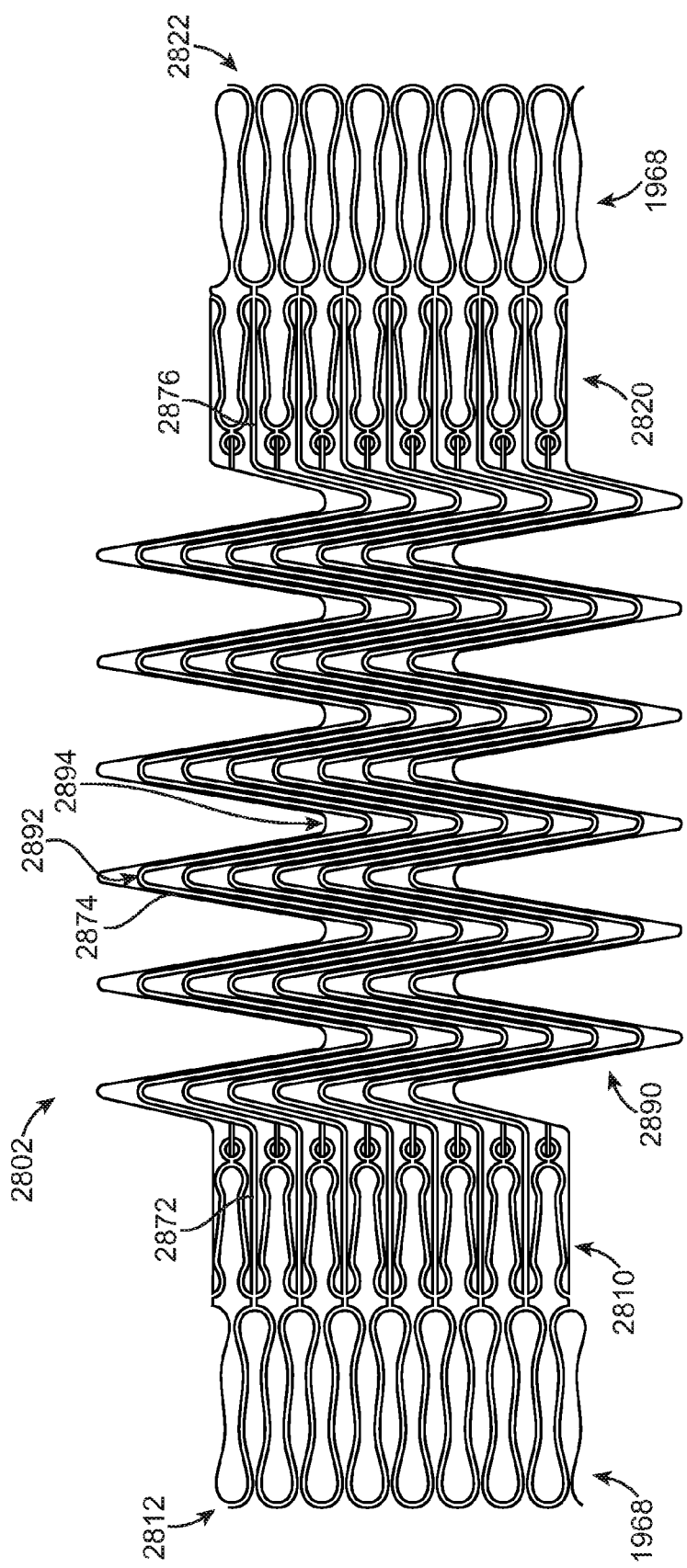
FIG. 28 is a laser-cut subcomponent for forming an exterior stent component according to another embodiment of the present invention.

FIG. 28 is a laser-cut subcomponent for forming an exterior stent component in accordance with another embodiment of the present invention. The laser cut subcomponent is shown in a schematic, showing the generally circular exterior stent component 2802 laid out flat, but one skilled in the art can appreciate that the subcomponent depicted therein is intended to be used as a cylindrical body. In this embodiment, the longitudinally-extending connectors are helical spars 2890 that nest within each other. More particularly, helical spars 2890 include a straight proximal section 2872, a wavelike or sinusoidal intermediate section 2874, and a straight distal section 2876. Wavelike or sinusoidal intermediate sections 2874 provide both additional surface area and pockets to allow for tissue in growth that will further aid in fixing the stent system to the vessel wall and avoid stent migration after deployment. Sinusoidal intermediate section 2874 includes a pattern of straight segments with crowns 2892 connecting adjacent straight segments. Valleys 2894 are the open curved or hollowed out portion formed by crowns 2892. Every other crown 2892 of a helical spar 2890 nests within a corresponding valley 2894 of an adjacent helical spar 2890. Straight proximal and distal sections 2872, 2876 have a length approximately equal to the length of a straight segment of stent struts 2810, 2820, while sinusoidal intermediate section 2874 has a length at least sufficient to connect proximal stent strut 2810 to distal stent strut 2820. Although the embodiment depicted in FIG. 28 includes flared stent segments 1968 at proximal end 2812 and distal end 2822 of exterior stent component 2802, it will be understood that helical spars 2890 may be used as the longitudinally-extending connectors for any embodiment of the exterior stent component described herein.

Figure 29:
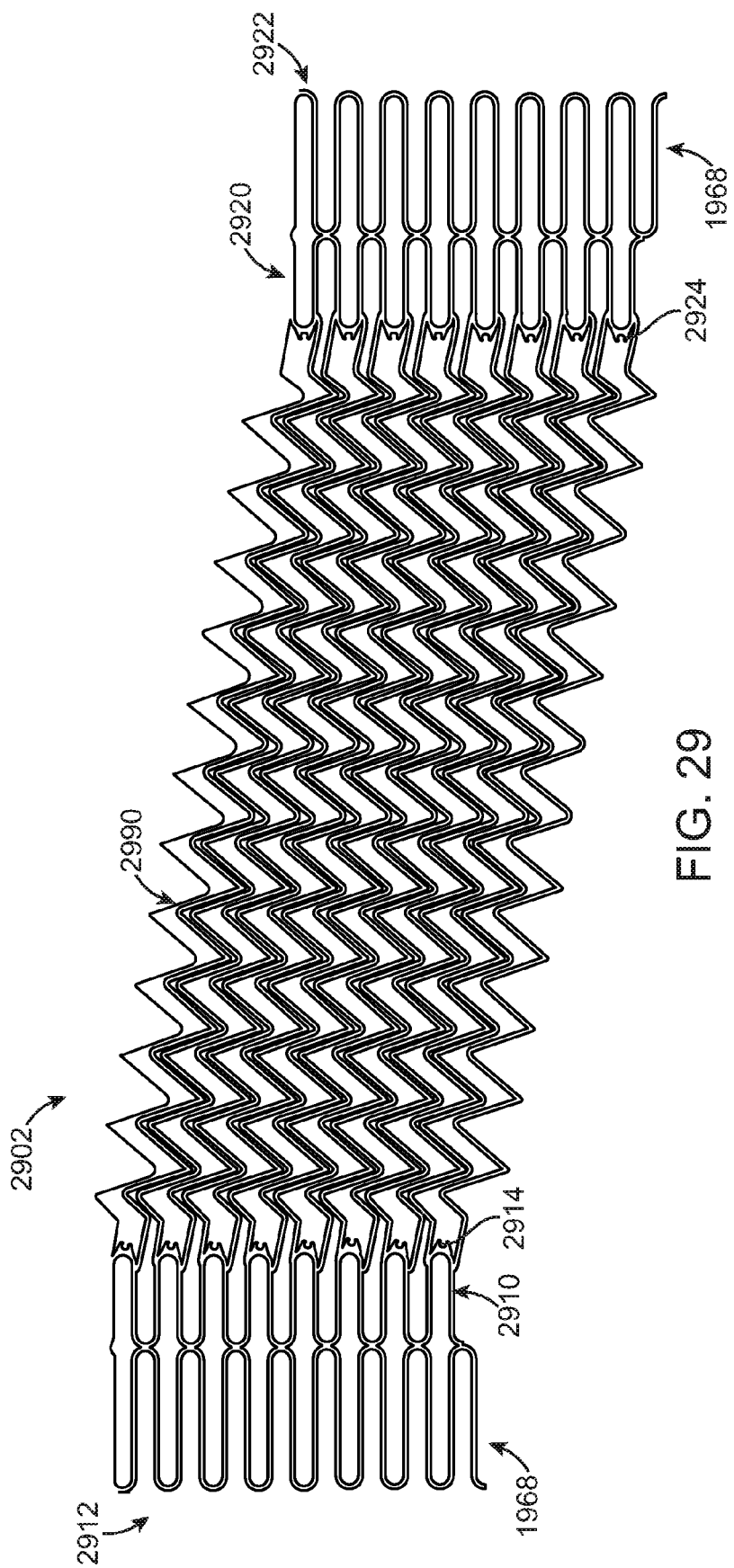
FIG. 29 is a laser-cut subcomponent for forming an exterior stent component according to another embodiment of the present invention.
Figure 30:
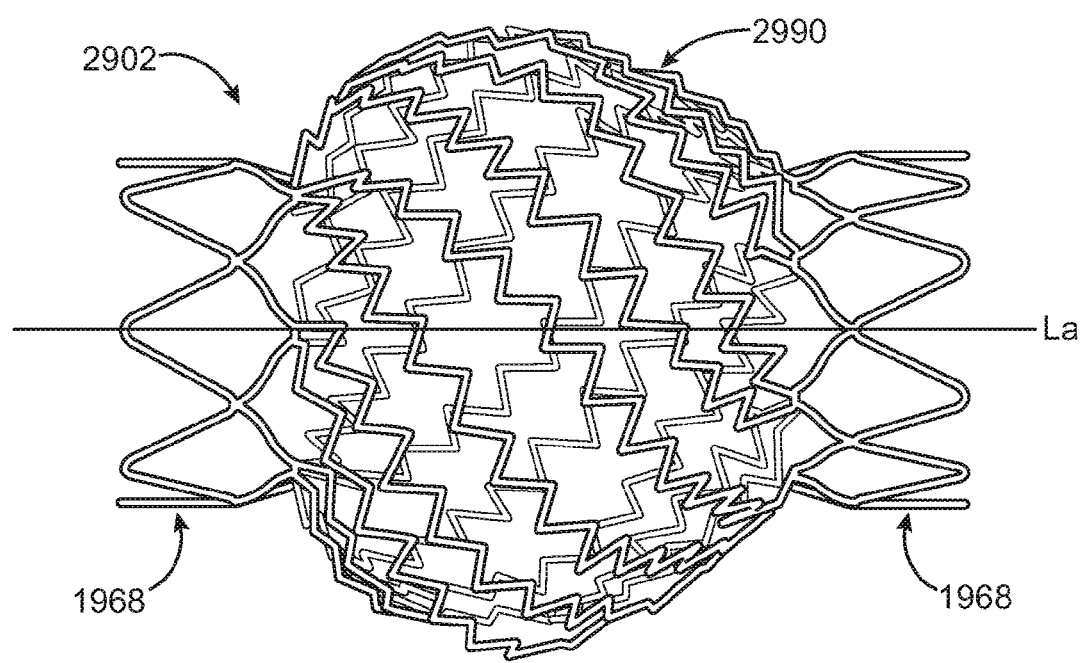
FIG. 30 is a side view of the exterior stent component formed according to the laser-cut subcomponent of FIG. 29.

FIG. 29 is a laser-cut subcomponent for forming an exterior stent component in accordance with another embodiment of the present invention, while FIG. 30 is a side view of the exterior stent component formed according to the laser-cut subcomponent of FIG. 29. The laser cut subcomponent is shown in a schematic, showing the generally circular exterior stent component 2902 laid out flat, but one skilled in the art can appreciate that the subcomponent depicted therein is intended to be used as a cylindrical body. Similar to the embodiment of FIG. 28, the longitudinally-extending connectors are helical spars 2990 that nest within each other in that the every other crown of a first helical spar nests within a corresponding valley of a second, adjacent helical spar. In the embodiment of FIG. 29, however, two nested helical spars 2990 extend between a crown 2914 of a proximal stent strut 2910 and a crown 2924 of a distal stent strut 2920. As such, twice as many longitudinally-extending connectors are provided in exterior stent component 2990 as in the exterior stent components depicted in the previous embodiments. For example, in the embodiment depicted in FIG. 29, a total of sixteen helical spars 2990 are provided between the proximal stent strut 2910 and distal stent strut 2920. The increased number of longitudinally-extending connectors assist in fixing the stent system to the vessel wall, and further provide additional radial support for the vessel. As shown in FIG. 30, helical spars 2990 do not extend generally parallel to longitudinal axis $L_a$ of the exterior stent component but rather wrap or spiral around longitudinal axis $L_a$, as well as the interior stent component, in a helical manner. A helical manner as used herein is intended to define a longitudinally-extending connector that starts at a proximal end of the stent system and ends at the distal end of the stent system at a predetermined angle from the longitudinal axis $L_a$ greater than zero. The predetermined angle of the helix reduces the amount that the longitudinally-extending connectors bulge/bow outwards upon expansion and foreshortening of the interior stent component. The outward bulge of the longitudinally-extending connectors can be achieved by including a wavelike or sinusoidal section along the length of the longitudinally-extending connector. The wavelike or sinusoidal section may be cut long and compressed prior to delivery so that the longitudinally-extending connectors can compensate for any lost advantage due to the reduced foreshortening of the interior stent component. In addition, the wavelike or sinusoidal sections provide both additional surface area and pockets to allow for tissue in growth that will further aid in fixing the stent system to the vessel wall and avoid stent migration after deployment. Although the embodiment depicted in FIGS. 29-30 includes flared stent segments 1968 at proximal end 2912 and distal end 2922 of exterior stent component 2902, it will be understood that helical spars 2990 may be used as the longitudinally-extending connectors for any embodiment of the exterior stent component described herein.

Figure 31:
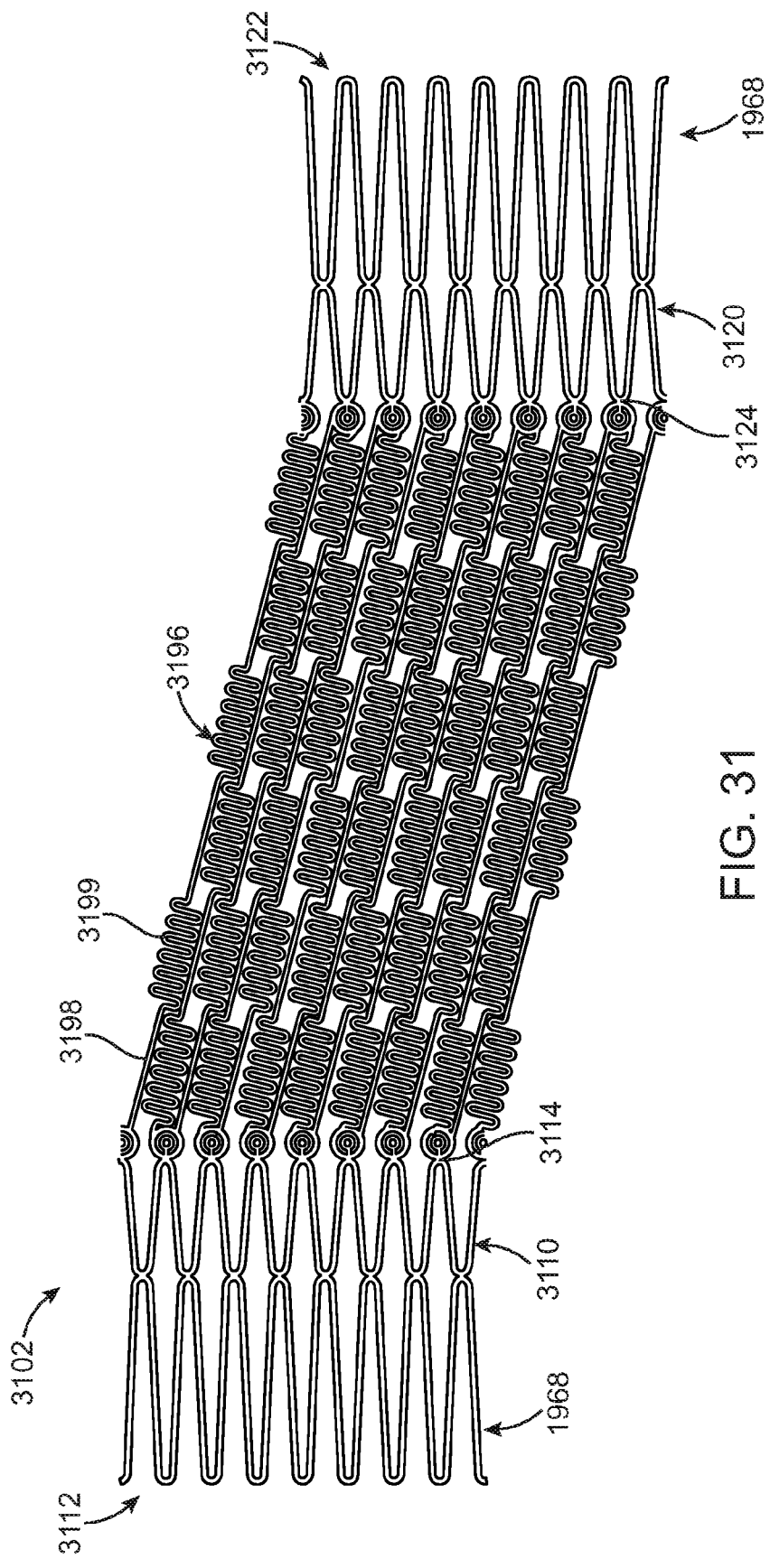
FIG. 31 is a laser-cut subcomponent for forming an exterior stent component according to another embodiment of the present invention.

FIG. 31 is a laser-cut subcomponent for forming an exterior stent component in accordance with another embodiment of the present invention. The laser cut subcomponent is shown in a schematic, showing the generally circular exterior stent component 3102 laid out flat, but one skilled in the art can appreciate that the subcomponent depicted therein is intended to be used as a cylindrical body. In this embodiment, the longitudinally-extending connectors are spars 3196 that coordinate with each other. More particularly, spars 3196 include alternating straight sections 3198 and wavelike or sinusoidal sections 3199. Sinusoidal sections 3199 of a first spar 3196 abut straight sections 3198 of a second, adjacent spar 3196. Similar to the embodiment of FIGS. 29-30, two spars 3196 extend between a crown 3114 of a proximal stent strut 3110 and a crown 3124 of a distal stent strut 3120 in order to increase the number of longitudinally-extending connectors provided in the exterior stent component. For example, in the embodiment depicted in FIG. 31, a total of sixteen helical spars 3196 are provided between the proximal stent strut 3110 and distal stent strut 3120. The increased number of longitudinally-extending connectors assists in fixing the stent system to the vessel wall, and further provides additional radial support for the vessel. Although the embodiment depicted in FIG. 31 includes flared stent segments 1968 at proximal end 3112 and distal end 3122 of exterior stent component 3102, it will be understood that spars 3196 may be used as the longitudinally-extending connectors for any embodiment of the exterior stent component described herein.

In previously-described embodiments, the exterior stent component is attached to the interior stent component. In other embodiments of the present invention, the exterior stent component may be captured or held loosely in place by the interior stent component such that the two components are in a "floating" arrangement. In such "floating" embodiments, the longitudinally-extending connectors of the exterior stent component may be threaded onto hooks attached to an outer surface of the interior stent component or may be woven through the openings between adjacent outermost stent struts of the interior stent component. Floating connections between the exterior stent component and the interior stent component provide more flexibility in shape conformance of the overall stent system than fixed or rigid connections. In addition, floating connections provides an even greater amount of mechanical isolation between an inner wall of the stent system, defined by an interior stent component, and an outer wall of the stent system, defined by an exterior stent component, than in previously-described embodiments. Mechanical isolation is important for a stent system that holds a secondary device having a fixed diameter, such as a valve, within a central flow lumen thereof because the mechanical isolation allows the fixed-diameter secondary device to be placed within a vessel of relatively larger size and/or irregular shape. The exterior stent component provide the required wall opposition forces while the mechanical influence to the interior stent component is minimized, thus reducing the possibility that the central flow lumen of the stent system, defined within the interior stent component, will be distorted in shape or size. In addition, the floating connections minimize stress points between the exterior stent component and the interior stent component, thus providing a longer life to the device. Floating connections may be located at both proximal and distal ends of the stent system, or may be utilized at only one end of the system while a fixed connection, such as that provided by welding, occurs at the other end of the system. In another embodiment, floating and fixed connections may vary from band to band.

Figure 39A:
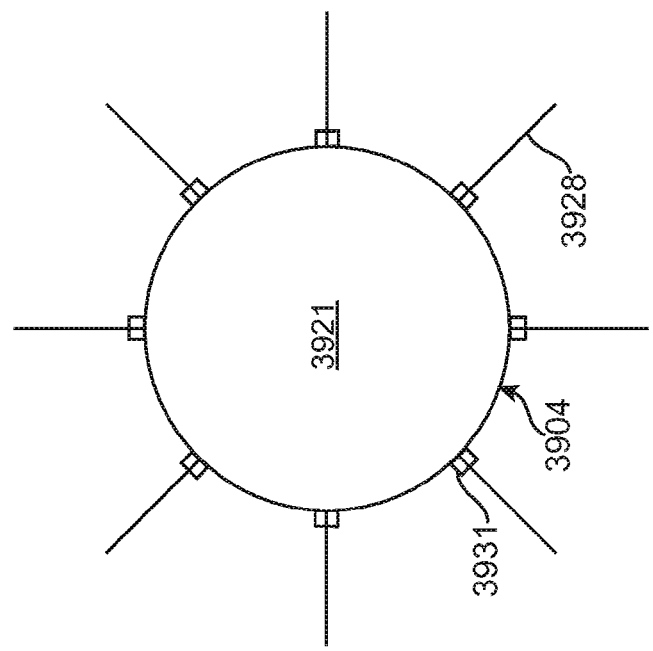
FIG. 39A is an end view of the floating double walled stent system of FIG. 39.
Figure 39:
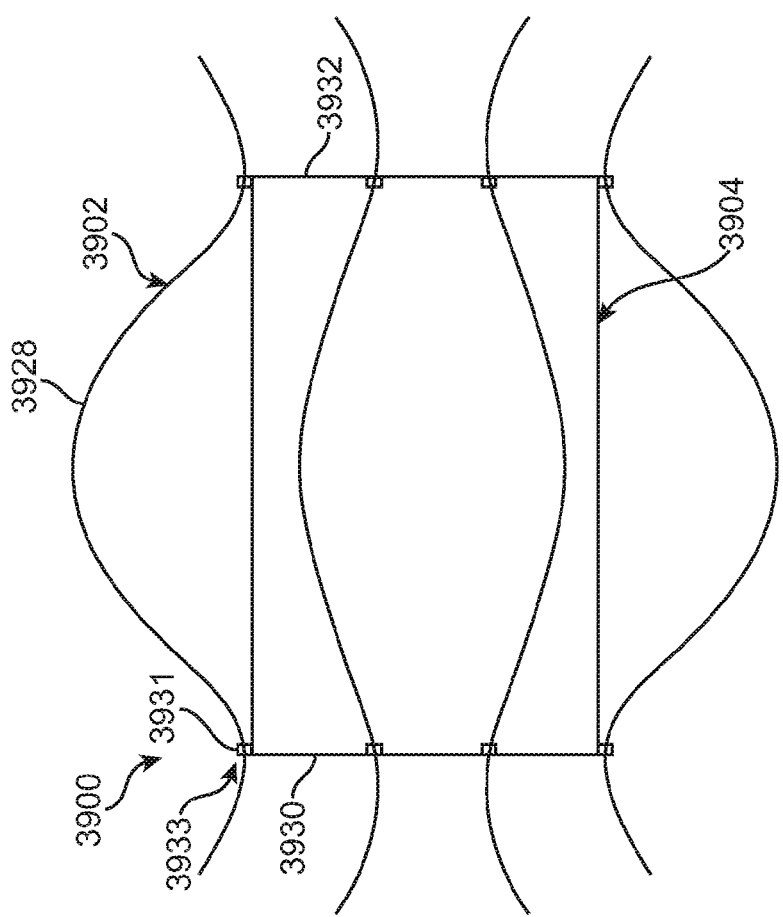
FIG. 39 is a side view of a floating double walled stent system according to an embodiment of the present invention, wherein the system is in an expanded configuration.

For example, FIGS. 39-39A illustrate a "floating" or slidable connection 3933 between an exterior stent component 3902 and an interior stent component 3904 of a double walled stent system 3900 according to another embodiment of the present invention. A plurality of longitudinally-extending bands or spars 3928 of exterior stent component 3902 are captured or held loosely in place by the interior stent component 3904, which permits interior stent component 3904 to "float" independently therefrom. Similar to previous embodiments, an outer surface of longitudinally-extending bands or spars 3928 of exterior stent component 3902 define an outer diameter of stent system 3900, while the cylindrically-shaped tubular body of interior stent component 3904 defines a central flow lumen 3921 having an inner diameter of stent system 3900. The central flow lumen 3921 has a consistent predetermined expanded diameter to accommodate blood flow there through. For example, the consistent predetermined expanded diameter may be approximately the same as the normal diameter of the body vessel in which the stent system is to be implanted. Interior stent component 3904 may be adapted from any appropriate stent configuration known to one of skill in the art and may include a valve located therein.

Interior stent component 3904 has a proximal end 3930 and a distal end 3932, each of which may include a plurality of hooks or loops 3931 around a circumference thereof. Each hook or loop 3931 is a strand or band of material having a first end and a second end, the first and second ends being connected to the outer surface of the interior stent component 3904 to define a receptacle. Alternatively, a single filament may be continuously woven around the circumference of the interior stent component to form the plurality of hooks or loops. Each band 3928 of exterior stent component 3902 is a slightly curved strip or plank of material that acts like a leaf spring when expanded. In the present embodiment, bands 3928 have a length that is greater than a length of the tubular body of interior stent component 3904. Each band 3928 is individually "threaded" or disposed through the receptacles defined by a set of corresponding hooks or loops 3931 of interior stent component 3904, one of which is located at proximal end 3930 and the other of which is located at distal end 3932. In this manner, a proximal end of each band 3928 extends proximally of proximal end 3930 of interior stent component 3904 and a distal end of each band 3928 extends distally of distal end 3932 of interior stent component 3904. The ends of bands 3928 are slightly curved in a radially outward direction such that bands 3928 have a sinusoidal shape in order to capture or contain exterior stent component 3902 within the plurality of hooks or loops 3931 during advancement and tracking to the treatment site. Bands 3928 may additionally or alternatively be contained within the plurality of hooks or loops 3931 by varying the size thereof such that a portion of each band includes a width that is too large to fit through the receptacles defined by hooks or loops 3931, or by varying the shape thereof such that a portion of each band includes a shape such as a zig-zag that is difficult or unlikely to pass through the receptacles defined by hooks or loops 3931, or by the addition of a separate piece of fabric or other matrix that is continuously woven around the circumference of interior stent component 3904 to span the gaps between individual bands 3928 in order stabilize the bands to the interior stent component. Interior stent component 3904 is centered inside of or within bands 3928 of exterior stent component 3902 but is not fixedly attached to exterior stent component 3902. Rather floating connection 3933 is present between the two components in which bands 3928 of exterior stent component 3902 are captured or held loosely in place by the plurality of hooks or loops 3931 located around the circumference of proximal end 3930 and distal end 3932 of interior stent component 3904. As such, interior stent component 3904 is allowed to "float" or move independently from exterior stent component 3902.

In previously-described embodiments in which the exterior stent component is fixedly attached to the interior stent component, the exterior stent component is deployed or radially expanded via foreshortening dynamics of the interior stent component. However, when in a "floating" arrangement, longitudinally-extending bands 3928 of exterior stent component 3902 are self-expanding and bow radially outward to come in contact with the vessel wall to aid in fixing stent system 3900 to the treatment site. For example, in one embodiment, deployment of self-expanding exterior stent component 3902 may be facilitated by utilizing shape memory characteristics of a material such as nickel-titanium (nitinol). Shape memory metals are a group of metallic compositions that have the ability to return to a defined shape or size when subjected to certain thermal or stress conditions. Shape memory metals are generally capable of being deformed at a relatively low temperature and, upon exposure to a relatively higher temperature, return to the defined shape or size they held prior to the deformation. This enables the stent component to be inserted into the body in a deformed, straighter state so that it assumes its "remembered" curved shape once it is exposed to a higher temperature, i.e., body temperature or heated fluid, in vivo. Once placed at the treatment or deployment site, the longitudinally-extending bands 3928 of exterior stent component 3902 resume their heat-shaped form and contact the vessel wall to provide the required opposition forces in the vessel.

In another embodiment, deployment of self-expanding exterior stent component 3902 may be facilitated by utilizing a self-expanding spring-type or superelastic material such as nickel-titanium (nitinol). Self-expanding exterior stent component 3902 may be collapsed or crimped from an expanded shape into the contracted or compressed configuration on a delivery catheter for delivery within the vessel. When a sleeve or sheath holding the stent system in the collapsed shape is removed, the exterior stent component 3902 assumes its expanded or deployed state at the treatment site within the vessel. Interior stent component 3904 may be balloon expandable or self-expanding. As in previous embodiments, an outer surface of interior stent component 3904 makes little to no contact with the vessel wall but rather remains centered inside exterior stent component 3902. Interior stent component 3904 is configured such that central flow lumen 3921 is radially centered within the vessel.

Figure 40A:
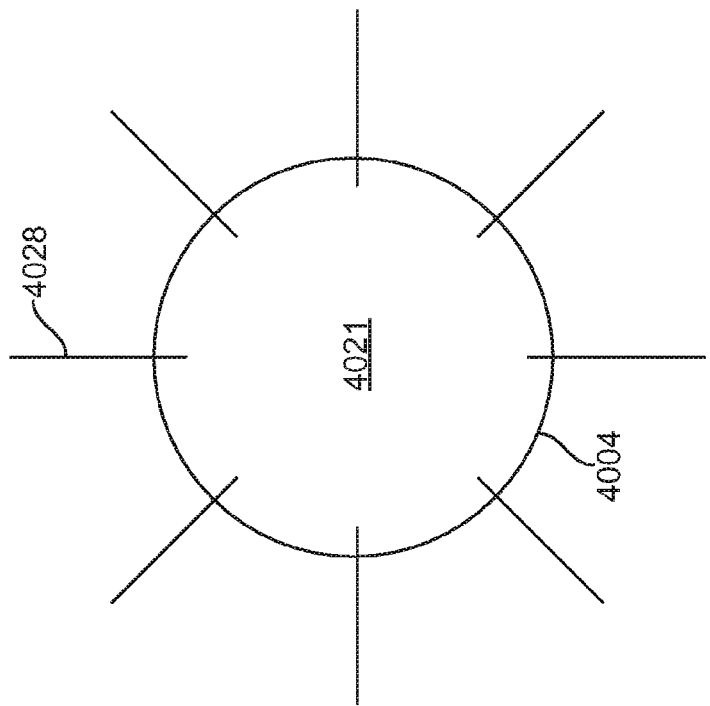
FIG. 40A is an end view of the floating double walled stent system of FIG. 40.
Figure 40:
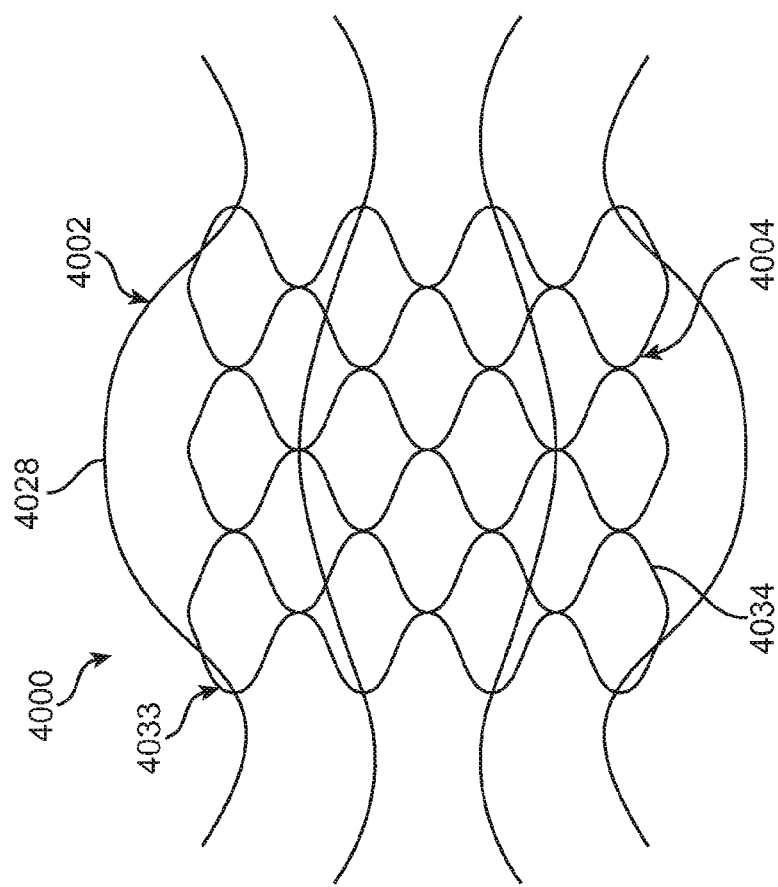
FIG. 40 is a side view of a floating double walled stent system according to another embodiment of the present invention, wherein the system is in an expanded configuration.

In another "floating" embodiment of the present invention, the longitudinally-extending connectors of the exterior stent component may be woven through the openings between outermost stent struts of the interior stent component. For example, FIGS. 40-40A illustrate "floating" or slidable connections 4033 between an exterior stent component 4002 and an interior stent component 4004. Similar to the above embodiments, longitudinally-extending bands or spars 4028 of exterior stent component 4002 define an outer diameter of stent system 4000. Interior stent component 4004, which may be adapted from any appropriate stent configuration known to one of skill in the art and may include a valve located therein, defines a central flow lumen 4021 of stent system 4000. A plurality of adjacent stent struts 4034 are aligned so as to form the cylindrically-shaped tubular body shape of interior stent component 4004. The plurality of longitudinally-extending bands or spars 4028 of exterior stent component 4002 are woven through openings between adjacent stent struts 4034 in order to form floating connections 4033. More particularly, a proximal portion of each of band 4028 is woven through an opening between adjacent stent struts 4034 at the proximal end of interior stent component 4004, and a distal portion of each of band 4028 is woven through an opening between adjacent stent struts 4034 at the distal end of interior stent component 4004. The ends of bands 4028 are slightly curved in a radially outward direction such that bands 4028 have a sinusoidal shape in order to capture or contain exterior stent component 4002 within openings defined by adjacent stent struts of interior stent component 4004 during advancement and tracking to the treatment site. Additionally, a separate piece of fabric or other matrix may be continuously woven around the circumference of interior stent component 4004 to span the gaps between individual bands 4028 in order stabilize the bands to the interior stent component. Bands 4028 of exterior stent component 4002 are self-expanding such as bands 3928 described above.

Figure 32:
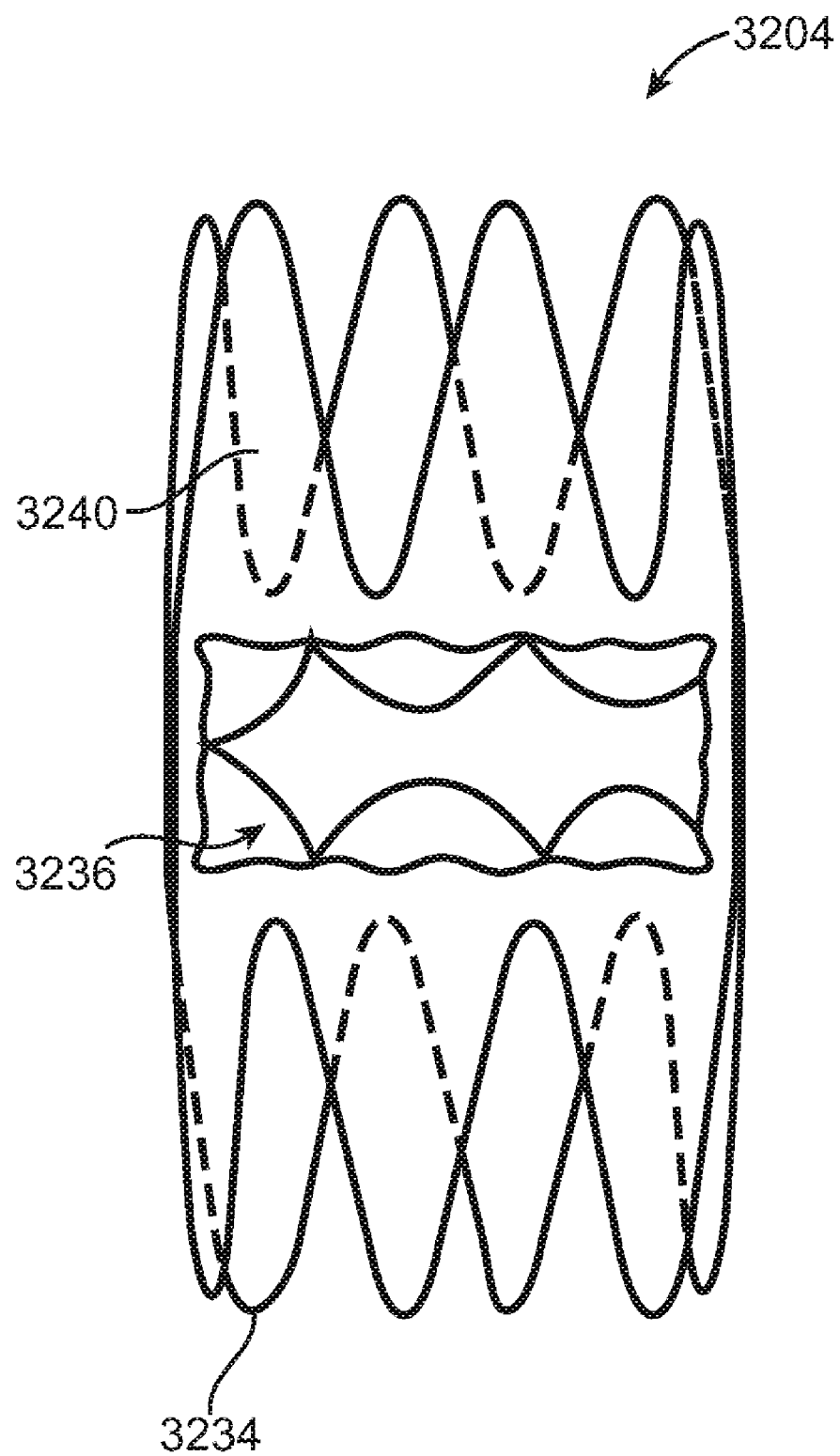
FIG. 32 shows interior stent component having a valve therein according to an embodiment of the present invention.

In any embodiment of the present invention, it should be understood that the interior stent component may include a valve therein to regulate flow there through. FIG. 32 shows an interior stent component 3204 having a valve 3236 therein capable of blocking flow in one direction. As described in previous embodiments of the interior stent component, interior stent component 3204 includes a plurality of adjacent stent struts 3234 aligned substantially parallel relative to longitudinal axis $L_a$ so as to form a cylindrically-shaped tubular body. In addition, interior stent component 3204 includes valve 3236 which is sealingly and permanently attached to the interior surface of interior stent component 3204 and/or graft material 3240 enclosing or lining the plurality of stent struts 3234 of interior stent component 3204. Valve 3236 may be a bovine or porcine valve treated and prepared for use in a human, or may be a mechanical valve or a synthetic leaflet valve. Graft material 3240 may be a low-porosity woven fabric, such as polyester, Dacron fabric, or PTFE, which creates a one-way fluid passage when attached to interior stent component 3204. For example, the interior stent component may consist of a percutaneously implanted bovine or porcine valve treated and prepared for use in a human and sewn inside a laser-welded stent such as that described in U.S. Pat. No. 5,957,949 titled "Percutaneous Placement Valve Stent" to Leonhardt et al., the contents of which are incorporated by reference herein in its entirety. The double walled stent system of the present invention is particularly suited for use in the right ventricular outflow tract because the exterior stent component allows for patient growth and/or adjusts to anomalies of a body lumen as explained above. Thus, when treating anomalies of the right ventricular outflow tract, it may be desirable to utilize a stented valve as the interior stent component. However, the double walled stent system of the present invention may also be utilized without a valve therein for treating any other medical conditions where it is deemed useful. Regardless of the specific configuration of the interior stent component, the exterior stent component bows radially outward to adjust to growth and/or anomalies of a body lumen and functions to secure the double walled stent system in place within the body lumen. As such, the interior stent component may be any appropriate stent known in the art as long as it is configured to be joined to the exterior stent component.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A stent system for use within a body lumen, the system comprising:
    an interior stent component having a proximal end, a distal end, and a generally tubular cylindrical body defining a central flow lumen there through; and
    an exterior stent component including a plurality of longitudinally-extending connectors, wherein the proximal and distal ends of the interior stent component are attached to the exterior stent component such that the longitudinally-extending connectors are radially positioned around the tubular body of the interior stent component,
    wherein when the stent system is in an expanded configuration the longitudinally-extending connectors of the exterior stent component bow radially outward away from the tubular body of the interior stent component to contact a vessel wall of the body lumen while the interior stent component remains radially centered within the longitudinally-extending connectors, and
    wherein foreshortening of the interior stent component reduces a length of the interior stent component between an unexpanded configuration and the expanded configuration of the stent system whereby proximal ends and distal ends of the longitudinally-extending connectors move closer together to bow the longitudinally-extending connectors radially outward.

2. The stent system of claim 1, wherein in the expanded configuration the longitudinally-extending connectors of the exterior stent component undergo greater radial expansion than the interior stent component such that the interior stent component makes little to no contact with the vessel wall.

3. The stent system of claim 1, wherein a proximal end of each longitudinally-extending connector is attached to the proximal end of the interior stent component and a distal end of each longitudinally-extending connector is attached to the distal end of the interior stent component such that the interior stent component is longitudinally centered between the proximal and distal ends of the longitudinally-extending connectors.

4. The stent system of claim 1, wherein the exterior stent component includes a proximal stent strut and a distal stent strut joined via the plurality of longitudinally-extending connectors, and wherein the proximal end of the interior stent component is attached to the proximal stent strut of the exterior stent component and the distal end of the interior stent component is attached to the distal stent strut of the exterior stent component such that the interior stent component is longitudinally centered between the proximal and distal stent struts of the exterior stent component.

5. The stent system of claim 4, wherein the proximal end of the interior stent component is welded to the proximal stent strut of the exterior stent component and the distal end of the interior stent component is welded to the distal stent strut of the exterior stent component, and the longitudinally-extending connectors of the exterior stent component remain detached from the tubular body of the interior stent component.

6. The stent system of claim 4, further including:
    a plurality of tabs formed on each of the proximal end and the distal end of the interior stent component; and
    a plurality of receptacles formed on an innermost end of each of the proximal stent strut and the distal stent strut of the exterior stent component, wherein each of the receptacles is configured to receive a corresponding tab, wherein the plurality of tabs are positioned within the plurality of receptacles to connect the exterior and interior stent components.

7. The stent system of claim 6, wherein each tab and receptacle is welded together.

8. The stent system of claim 6, wherein each tab and receptacle is cryogenically coupled together.

9. The stent system of claim 4, wherein the exterior stent component includes a first flared stent strut attached to a proximal end of the proximal stent strut and a second flared stent strut attached to a distal end of the distal stent strut.

10. The stent system of claim 9, wherein the first and second flared stent struts form approximately a twenty degree angle with a longitudinal axis of the exterior stent component.

11. The stent system of claim 1, wherein the longitudinally-extending connectors are generally straight bands of material along an entire length thereof.

12. The stent system of claim 11, wherein a first longitudinally-extending connector has a first width and a second longitudinally-extending connector has a second width, wherein the first width is greater than the second width.

13. The stent system of claim 1, wherein at least one of the longitudinally-extending connectors includes a sinusoidal section of material.

14. The stent system of claim 13, wherein the at least one longitudinally-extending connector includes a plurality of sinusoidal sections separated by straight sections.

15. The stent system of claim 1, wherein the longitudinally-extending connectors extend generally parallel to a longitudinal axis of the exterior stent component.

16. The stent system of claim 1, wherein the longitudinally-extending connectors are angled with respect to a longitudinal axis of the exterior stent component.

17. The stent system of claim 1, wherein the longitudinally-extending connectors extend in a helical fashion around a longitudinal axis of the exterior stent component.

18. The stent system of claim 1, further comprising:

a tether laterally connecting a first longitudinally-extending connector and a second longitudinally-extending connector.

19. The stent system of claim 1, further comprising:

a valve located within the central flow lumen of the interior stent component, wherein nonporous graft material covers at least a portion of the interior stent component.

* * * * *